(12) United States Patent
Dadachanji et al.

(10) Patent No.: US 12,343,743 B2
(45) Date of Patent: Jul. 1, 2025

(54) LIQUID PUMP DISPENSER INCLUDING A VIAL ADAPTER

(71) Applicant: KAIRISH INNOTECH Private Ltd., Mumbai (IN)

(72) Inventors: Rishad Kairus Dadachanji, Mumbai (IN); Pratul Prakash Potdar, Daman and Diu (IN); Keyurkumar Arvindbhai Patel, Daman & Diu (IN); Krupal Ashokbhai Chudasma, Gujarat (IN)

(73) Assignee: KAIRISH INNOTECH Private Ltd., Mumbai (IN)

( * ) Notice: Subject to any disclaimer, the term of this patent is extended or adjusted under 35 U.S.C. 154(b) by 31 days.

(21) Appl. No.: 17/999,968

(22) PCT Filed: Jul. 1, 2022

(86) PCT No.: PCT/IN2022/050604
§ 371 (c)(1),
(2) Date: Nov. 28, 2022

(87) PCT Pub. No.: WO2023/275899
PCT Pub. Date: Jan. 5, 2023

(65) Prior Publication Data
US 2024/0245580 A1    Jul. 25, 2024

(30) Foreign Application Priority Data
Jul. 1, 2021  (IN) .............................. 202121029684

(51) Int. Cl.
*B05B 11/10*  (2023.01)
*A61J 1/14*   (2023.01)

(52) U.S. Cl.
CPC .......... *B05B 11/1018* (2023.01); *A61J 1/1481* (2015.05); *B05B 11/1047* (2023.01); *A61J 1/1406* (2013.01)

(58) Field of Classification Search
CPC ............. B05B 11/1047; B05B 11/1001; B05B 11/0054; B05B 11/1018; B05B 15/30; A61M 11/00; A61M 11/007; A61J 1/1481
See application file for complete search history.

(56) References Cited

U.S. PATENT DOCUMENTS

| 4,277,001 A | 7/1981 | Nozawa |
| 4,775,079 A | 10/1988 | Grothoff |

(Continued)

FOREIGN PATENT DOCUMENTS

| CN | 102791385 A | 11/2012 |
| CN | 106794924 A | 5/2017 |

(Continued)

OTHER PUBLICATIONS

Second Office Action for corresponding Indian Application No. 202317002495 dated Dec. 16, 2023.

(Continued)

*Primary Examiner* — Ariana Zimbouski
(74) *Attorney, Agent, or Firm* — Renner, Otto, Boisselle & Sklar, LLP

(57) ABSTRACT

A liquid pump dispenser includes a vial adapter connected with a pump dispenser unit including a piston-type dispenser pump. When the vial adapter is coupled to the neck of a medical vial by latching, a piercing mandrel pierces a stopper sealing the vial. A fluid-tight communication between the vial adapter and pump dispenser unit is established by a flexible connecting tube, which helps to compensate mechanical tolerances and any misalignment or between the vial adapter and pump dispenser unit during (Continued)

assembly or use. The liquid pump dispenser can be used in an upside-down orientation of the medical vial without problems such as leakage or dripping at an outlet nozzle, and ensures a precise dosage of the liquid pumped from the medical vial. The vial adapter together with the pump dispenser unit can be pre-assembled and packaged as a unit.

20 Claims, 17 Drawing Sheets

(56) References Cited

U.S. PATENT DOCUMENTS

| | | | |
|---|---|---|---|
| 4,986,453 | A | 1/1991 | Lina et al. |
| 5,176,654 | A | 1/1993 | Schreiber |
| 5,222,636 | A | 6/1993 | Meuresch |
| 5,324,258 | A | 6/1994 | Rohrbough |
| 5,353,969 | A | 10/1994 | Balderrama |
| 5,397,303 | A | 3/1995 | Sancoff et al. |
| 5,478,337 | A | 12/1995 | Okamoto et al. |
| 6,050,459 | A * | 4/2000 | Johnson ............... B05B 15/30 222/530 |
| 6,158,676 | A | 12/2000 | Hughes |
| 6,258,078 | B1 | 7/2001 | Thilly |
| 6,269,976 | B1 * | 8/2001 | DeJonge ............... B67B 7/26 222/83.5 |
| 6,299,023 | B1 | 10/2001 | Amnone |
| 6,338,422 | B1 | 1/2002 | DeJonge |
| 6,776,312 | B2 * | 8/2004 | Masuzzo ............ B05B 11/0072 222/321.7 |
| 6,913,169 | B2 | 7/2005 | Lee |
| 7,389,947 | B2 | 6/2008 | Denton |
| 8,210,166 | B2 | 7/2012 | Denton et al. |
| 8,684,992 | B2 | 4/2014 | Sullivan et al. |
| 8,684,994 | B2 | 4/2014 | Lev et al. |
| 9,266,135 | B2 | 2/2016 | Harms et al. |
| 9,339,438 | B2 | 5/2016 | Lev et al. |
| 9,364,842 | B2 | 6/2016 | Petit |
| 10,426,702 | B2 | 10/2019 | Henninger et al. |
| 10,654,051 | B2 | 5/2020 | Meshberg |
| 2003/0155379 | A1 | 8/2003 | Masuzzo et al. |
| 2004/0134494 | A1 | 7/2004 | Papania et al. |
| 2007/0051831 | A1 | 3/2007 | Kuo |
| 2007/0079894 | A1 | 4/2007 | Kraus et al. |
| 2011/0223116 | A1 | 9/2011 | Century |
| 2013/0068797 | A1 | 3/2013 | Laidler et al. |
| 2014/0069961 | A1 | 3/2014 | Harms et al. |
| 2017/0128966 | A1 | 5/2017 | Law et al. |
| 2018/0339893 | A1 * | 11/2018 | Böhm ................ B05B 11/1004 |
| 2019/0290543 | A1 | 9/2019 | McKinnon et al. |
| 2020/0222629 | A1 | 7/2020 | Deng |
| 2020/0398005 | A1 * | 12/2020 | Simpson ............ B05B 11/1007 |

FOREIGN PATENT DOCUMENTS

| | | |
|---|---|---|
| CN | 105270729 B | 8/2017 |
| DE | 102011106261 A1 | 11/2012 |
| DE | 102011122211 A1 | 6/2013 |
| EP | 713409 B1 | 12/2001 |
| JP | 2011246135 A | 12/2011 |
| JP | 5472918 B2 | 2/2014 |
| JP | 5502579 B2 | 3/2014 |
| JP | 5875617 B2 | 1/2016 |
| WO | 2013093908 A1 | 6/2013 |
| WO | 2018149015 A1 | 8/2018 |

OTHER PUBLICATIONS

First Office Action for corresponding Chinese Application No. 202280045709.6 dated Jun. 12, 2024 and its English Machine Translation.
PCT/IN2022/050604; International Search Report and Written Opinion of the International Searching Authority dated Oct. 11, 2022.
First Office Action for corresponding Indian Application No. 202317002495 dated Feb. 28, 2023.
Communication under Rule 71(3) EPC in corresponding European Application No. 22747456.6 dated Mar. 29, 2023.

* cited by examiner

LIQUID PUMP DISPENSER INCLUDING A VIAL ADAPTER

This application is a national phase of International Application No. PCT/IN2022/050604 filed 1 Jul. 2022, which claims priority to India application No. 202121029684 filed 1 Jul. 2021, which is hereby incorporated herein by reference in its entirety.

FIELD OF INVENTION

The present invention generally relates to drug delivery devices for dispensing liquids from medical containers, and more specifically relates to a liquid pump dispenser including a vial adapter, which can be used to spray the contents of a medical vial as a fine mist in a sanitary, convenient and easy fashion without leakage. Moreover, the present invention relates to a vial adapter configured to be coupled to a pump dispenser unit and a medical vial, and the use of such a vial adapter.

BACKGROUND OF INVENTION

Pump-atomizing dispensers are well-known from the prior art and disclosed e.g., by US 20070051831 A1, U.S. Pat. No. 6,776,312 B2 and U.S. Pat. No. 5,176,654 A. For an efficient liquid transfer, the inlet tubes of such pump dispensers dip deep into the inner volume of the vial. When not coupled to the vial, the inlet tubes of such pump dispensers protrude over quite a significant length from the main body of the pump dispenser. As such inlet tubes need to be quit long, this makes a packaging under sterile conditions difficult.

U.S. Pat. No. 8,210,166 B2 discloses a multi-access adapter operable to dispense doses of a medicament in succession from a bulk container, such as a vial. The adapter may be used alone, or in combination with various discharge devices. One embodiment uses a compact vial adapter that can be locked onto the front end of a vial by means of a snap ring and which comprises a piercing mandrel that dips into the inner volume of a vial only over a short distance. The vial adapter has a first port configured to be coupled to a medical syringe and a second port, on an end of the vial adapter opposite to the first port, that can be coupled to a spraying nozzle. Operating the piston of the syringe causes the contents of the vial sprayed as a fine mist. All three components, namely the vial, the vial adapter and the syringe, can be packaged under sterile conditions, e.g. in a blister package. However, operation of the adapter may be a little cumbersome, because the liquid cannot be pumped out of the vial by a pump dispenser, and packaging all three components in separate sterile packaging units results in additional waste and higher costs for packaging, which is not desirable.

U.S. Pat. No. 6,269,976 B1 discloses a vial access spike adapter for a pump dispenser, comprising a hollow tubular body defining a cylindrical cavity inside, a thread for connecting the vial adapter with the pump dispenser, a snap ring for connecting the vial adapter with a medical vial, and a partition wall separating the cavity into a two half-spaces. A piercing mandrel for piercing a stopper of the vial for liquid transfer is disposed on the partition wall. The inlet tube of the pump dispenser is relatively long and protrudes over quite a significant length from the main body of the pump dispenser so that it can dip deep into the inner volume of the vial when the vial adapter is locked on the front end of the vial. This makes a packaging of the pump dispenser or of the pump dispenser together with the vial adapter under sterile conditions difficult.

However, for the transfer of liquid medical solutions, such as drug solutions or liquids including a vaccine, at least the transfer device for liquid transfer out of the vial and the components required for coupling the transfer device with a medical vial, need to be packaged under sterile conditions, whereas the upper surface of the elastomeric stopper of a vial could be disinfected prior to actual use, e.g., by a swab. Ensuring sterile conditions makes, however, the handling of such transfer devices and components difficult.

Manually operated spray pumps generally use a metal ball for closing and opening the bottom entrance of a pump housing to vary the pressure in the interior of the pump housing during pumping of a fluid. However, the metal ball fails to entirely close the pump housing bottom entrance because of its spherical shape and cannot rapidly respond to the variation of pressure of the pump housing's interior, resulting in leakage by dripping at the nozzle and the leakage of fluid owing to a small gap between the metal ball and the bottom entrance of the pump housing and hence the slow loss of pressure from the pump housing's interior. In addition, the metal ball acts to close the pump housing bottom entrance by gravity upon application of a downward force to the push button, and open it in response to loss of pressure in the pump housing's interior upon release of the downward force; however, the density of fluid present in the pump housing's interior increases upon application of the downward force to the push button and thus the relative gravity of the metal ball decreases, making the rapid closing of the pump housing bottom entrance difficult. Therefore, owing to the pressure loss in the pump housing's interior and the slow response to the variation of pressure, a leakage by dripping occurs at the initial step and final step of a spraying procedure.

If such manually operated spray pumps are used in an upside-down configuration of the vial, gravity will tend to displace the metal ball from the entrance of the pump housing or from a metal spring used as a resetting member a little. This may result in an additional leakage and dripping at the nozzle, making a precise dosage of the fluid by actuating the push button impossible.

SUMMARY OF INVENTION

The present invention is to at least alleviate the aforementioned effects by providing a liquid pump dispenser and a vial adapter to thereby offer simple and low-cost solutions for enabling the transfer of a liquid out of a medical vial and spraying the liquid as a fine mist in a sanitary, convenient and easy fashion without leakage.

According to the present invention there is provided a liquid pump dispenser, for pumping a dosage of liquid from a necked vial, which is sealed by a stopper, to an outlet in an upside-down orientation of the vial, the liquid pump dispenser comprising a vial adapter and a pump dispenser unit. The vial adapter is configured to be fixedly connected to the pump dispenser unit and to be coupled to the neck of a medical vial by latching. The vial adapter comprises a piercing mandrel configured for piercing a stopper of the vial for liquid transfer, when the vial adapter is coupled to the neck of a medical vial. The piercing mandrel is relatively short so that it will only protrude a little distance into the interior of a medical vial.

The pump dispenser unit is of a piston-type and comprises a ball-less pump actuated by a moveable operating button.

The piston-type pump dispenser unit enables a precise and repeatable dosage of the liquid pumped out of the medical vial in an upside-down (inverted) orientation of the medical vial, without the problems of leakage and dripping at an outlet nozzle.

According to the present invention, the vial adapter and the pump dispenser unit are connected with each other for liquid transfer via a flexible connecting tube. While the vial adapter and the key elements of the pump dispenser unit are made of a relatively stiff plastic material, in particular using injection molding techniques, the connecting tube will be made of a different plastic or polymeric material that is less stiff and flexible. The flexible connecting tube may thus serve to compensate any misalignment or relative displacement between the vial adapter and pump dispenser unit during assembly or use. It thus enables a reliable operation of the liquid pump dispenser without leakage. Moreover, assembly of the liquid pump dispenser is significantly facilitated, because the two main parts, namely the vial adapter and the pump dispenser unit, can be connected with each other without the need of a precise pre-alignment of these two parts and any misalignment can be compensated by the flexible connecting tube. Moreover, the flexible connecting tube may also assist in absorbing any axial stress or load acting on the vial adapter and/or pump dispenser unit during assembly or later use, particularly when the push button of the pump dispenser unit is pushed.

As the flexible connecting tube will be housed inside the vial adapter, the vial adapter together with the pump dispenser unit can be pre-assembled and packaged as a unit (liquid pump dispenser), to be delivered to customers as a ready-to-use unit that simply needs to be coupled to a vial by pushing and latching the second end of the vial adapter on the front end of a medical vial for liquid transfer. This significantly eases use of such liquid pump dispensers. Because neither the connecting tube nor the front end of the piercing mandrel protrudes beyond a bottom end of such a unit, the unit may also be packaged reliably in a simple and cost-effective manner according to the present invention, in particular in a simple pouch or packaging sealed by a thin plastic foil, wherein thin foils used for the packaging will not be damaged by the piercing mandrel or any other parts of the unit consisting of the pump dispenser unit coupled to the vial adapter. But the vial adapter itself also can be packaged reliably and in a simple and cost-effective manner according to the present invention, because also the piercing mandrel does not protrude beyond the bottom edge of the vial adapter. There will also be no risk that the front end of the connecting tube or piercing mandrel will be damaged during transport or storage, because it will not be exposed but protected by the perimeter of the afore-mentioned unit or vial adapter.

As the functions of piercing the vial stopper and supplying liquid to the pump dispenser unit are decoupled according to the present invention, each of the two members can be designed specifically and more efficiently for the desired purpose according to the present invention.

According to a further embodiment, the vial adapter comprises a hollow tubular body having a first end and a second end opposite to the first end, a cavity formed inside the hollow tubular body, a first connecting structure at the first end, configured for connecting the vial adapter with the pump dispenser unit, a second connecting structure at the second end, configured for latching the vial adapter at a neck of the vial, for connecting the vial adapter with the vial, a partition wall provided inside the hollow tubular body, which separates the cavity into a first half-space and a second half-space, a piercing mandrel configured for piercing a stopper of the vial for liquid transfer, which is disposed on the partition wall in the second half-space and comprises a cannula being in fluid communication with the first half-space, and a first tube coupling structure provided on the partition wall in the first half-space.

According to a further embodiment, the pump dispenser unit comprises a collar having a connecting structure mated to the first connecting structure of the vial adapter, for connecting the pump dispenser unit with the vial adapter, a central pump housing disposed in the collar, which defines a piston chamber, in which a piston is movably supported, a second tube coupling structure provided on the upper end of the central pump housing, and an operating button disposed below the pump housing, for actuating the piston, said operating button being biased towards a home position and being movable relative to the collar against a resilient resetting force.

It is the main purpose of the first and second connecting means to accomplish a stable and reliable coupling or connection of the vial adapter with the pump dispenser unit and vial adapter, respectively, and generally any kind of coupling may be used for this purpose. E.g., the coupling may be accomplished by threading, clamping, bonding or locking in a positive-fit manner or with frictional fit. Preferably, at least the coupling of the vial adapter with the pump dispenser unit is reversible, so that the pump dispenser unit may also be removed from the vial adapter for later re-use. Preferably, the pump dispenser unit is threaded on the first end of the vial adapter, whereas the vial adapter is preferably mechanically locked onto the front end of the medical vial, more specifically on the neck of the medical vial. The partition wall is formed as a disk or plate of uniform thickness that is closed except a central hole, which serves to connect the connecting tube with the cannula of the piercing mandrel. The first half-space is of cylindrical shape and the first coupling structure is disposed in the center and at the bottom of the first half-space, on a first surface of the partition wall. The first coupling structure is long enough and properly configured to establish the fluid-tight coupling with the flexible connecting tube so that no liquid is inadvertently spoiled inside the vial adapter, which facilitates later disposal of the vial adapter.

According to a further embodiment, a respective front end of the flexible connecting tube is accommodated in at least one of the first tube coupling structure and second tube coupling structure in a fluid-tight manner.

Generally, the connecting tube may be integrally formed with the vial adapter or pump dispenser unit, using e.g., 2K-injection molding techniques, allowing the connecting tube to be formed of a softer plastic material so that it is sufficiently flexible. However, according to a preferred embodiment of the present invention, the connecting tube is a separate member that is not integrally formed with the vial adapter or pump dispenser unit. Before final assembly of the liquid pump dispenser, the connecting tube first needs to be inserted into the tube coupling structure of the vial adapter or pump dispenser unit, which can be easily be accomplished during assembly of the liquid pump dispenser.

According to a further embodiment, the first and second tube coupling structure each comprises a cylindrical sidewall forming a cylindrical cavity of a width corresponding to an outer diameter of the connecting tube, for accommodating a respective front end of the connecting tube in a fluid-tight manner. Preferably, an outer diameter of the connecting tube may be slightly larger than an inner width (diameter) of the first and second tube coupling structure, so that the connecting tube is slightly compressed in the first and second tube coupling structure, which enhances the fluid-tight sealing effect.

According to a further embodiment, an upper edge on the inner surface of the cylindrical wall may be beveled inward, for guiding a respective bottom end of the connecting tube into the respective cylindrical cavity. This further assists in preventing damage of the connecting tube when coupling the pump dispenser unit with the vial adapter, because the front end of the connecting tube may gently slide into the cylindrical cavity of the respective tube coupling structure.

According to a further embodiment, a height of the cylindrical cavity formed by the respective cylindrical side-wall may be dimensioned such that a free space remains between the front end of the connecting tube and an upper surface of the partition wall and/or upper end of the central pump housing, when the pump dispenser unit is coupled to the vial adapter. This helps to further compensate for manufacturing tolerances, any misalignment between vial adapter and pump dispenser unit and loads acting on any of these units when the operating button is actuated.

According to a further embodiment, a wall thickness of the respective front end of the connecting tube may be smaller to form a lower portion of the connecting tube so that the connecting tube can slide even more gently into the respective cylindrical cavity for liquid-tight coupling. Moreover, the height of the cylindrical cavity formed by the respective cylindrical side-wall may be dimensioned such that the respective end of the connecting tube does not completely dip into the respective cylindrical cavity when the pump dispenser unit is coupled to the vial adapter, which may further assist for compensation of manufacturing tolerances and the like.

According to a further embodiment, a finger-rest may be provided on and formed integral with an outer surface of the hollow tubular body, which protrudes outward in radial direction from the outer surface of the hollow tubular body. During use, when both the pump dispenser and the vial is coupled to the vial adapter, the finger-rest will be positioned automatically at a central position, in-between the vial and pump dispenser, which significantly enhances an ergonomic operation of the pump dispenser. Preferably, the finger-rest is provided at a position, which will be close to the bottom end of the pump dispenser when coupled with the vial adapter.

According to a further embodiment, the finger-rest may comprise two wing-shaped protrusions provided on diametral opposite sides on the outer surface of the hollow tubular body. During use the pump dispenser may thus be operated easily in the upside-down orientation of the medical vial by grasping the finger-rest with the forefinger and middle finger and pushing a button of the pump dispenser with a thumb, to spray the contents of a medical vial via an outlet of the pump dispenser.

According to a further embodiment, the piercing mandrel does not protrude beyond the second end of the vial adapter. Hence, also the vial adapter itself can be packaged reliably and in a simple and cost-effective manner. There will be no risk that the front end of the piercing mandrel will be damaged during transport or storage, because it will not be exposed but protected by the perimeter of the afore-mentioned unit or vial adapter. Moreover, the vial adapter can be packaged reliably in a simple and cost-effective manner, in particular in a simple pouch or packaging sealed by a thin plastic foil, wherein thin foils used for the packaging will not be damaged by the piercing mandrel.

According to a further embodiment, the second connecting means may comprise a plurality of resilient legs disposed along a circumference of the vial adapter at the second end at equiangular spacing and spaced apart to each other via axial slots, wherein the resilient legs each comprise a protrusion beveled inward into the second half-space. Thus, the vial adapter can simply be locked by positive-fit on the front end or neck of the vial, with the protrusions embracing a bottom of the rolled edge of the vial in the locked position. A height, where an inner diameter of a circle formed by the beveled protrusions corresponds to an outer diameter of a cap provided on a front end or neck of the vial, may correspond to or preferably is a little less than the height of a front end of the piercing mandrel above the second end of the vial adapter. Thus, the vial adapter will be automatically centered on the vial first, before the piercing mandrel will start piercing the vial stopper, when the vial adapter is locked to the front end of a vial.

According to a further embodiment, the height of the front end of the piercing mandrel above the second end of the vial adapter may be in the range of 0.4 to 2.0 mm, more preferably in the range of 0.4 to 1.0 mm. These parameter ranges turned out to be ranges enabling a particular efficient automatic centering of the vial adapter and piercing mandrel at the beginning of coupling the vial adapter to the front end of a vial by simply pushing the vial adapter onto the vial.

According to a further embodiment, an efficient automatic centering of the vial adapter and piercing mandrel can be accomplished when the height of the front end of the piercing mandrel above the level, where the inner diameter of a circle formed by the beveled protrusions corresponds to the outer diameter of the cap provided on a front end of the vial, is in the range of 0.4 to 2.0 mm, more preferably in the range of 0.4 to 1.0 mm.

According to a further embodiment, the piston of the pump dispenser unit is supported on the operating button and a sealing member is supported on the piston; wherein, in the home position of the operating button, the inlet of the piston chamber is in fluid communication with an upper portion of the piston chamber via an upper transfer channel, and, when the operating button is pushed from the home position towards the collar against the resilient resetting force, the upper transfer channel is sealed against the inlet of the piston chamber by an upper end of the sealing member while the piston chamber remains in fluid communication with the outlet of the pump housing via a transfer channel formed between the sealing member and an inner side-wall of the piston chamber. The dosage expelled is thus precisely defined by the volume of the pump housing.

According to a further embodiment, the upper end of the sealing member is formed by a cylindrical side-wall, and a cylindrical partition wall is provided at an upper end of the piston chamber, to form a cylindrical slot of a width corresponding to the width of the cylindrical side-wall of the sealing member, wherein the upper transfer channel is a narrow gap between the cylindrical side-wall of the sealing member and the cylindrical partition wall, when the operating button is in the home position.

According to a further embodiment, a bottom end of the sealing member is a cylindrical protrusion, which is accommodated in a central bore of the piston so as to be stationary relative to the piston, According to a further embodiment, the operating button is in fluid communication with the outlet and with an outlet of the pump housing, and the pump dispenser unit comprises a tube that is pivotably supported on the operating button or on a main body of the pump dispenser unit, wherein the outlet is a spraying nozzle for spraying the liquid pumped out of the vial.

According to a further embodiment, the liquid pump dispenser may be sealed, preferably under sterile conditions, in a pouch, container or blister package including a plastic packaging foil.

OVERVIEW ON DRAWINGS

The invention will now be described by way of example and with reference to the accompanying drawings, from which further features, advantages and problems to be solved will become apparent. In the drawings.

In the drawings, the same reference numerals designate identical or substantially equivalent elements or groups of elements.

DETAILED DESCRIPTION OF PREFERRED EMBODIMENTS

Figure 2:
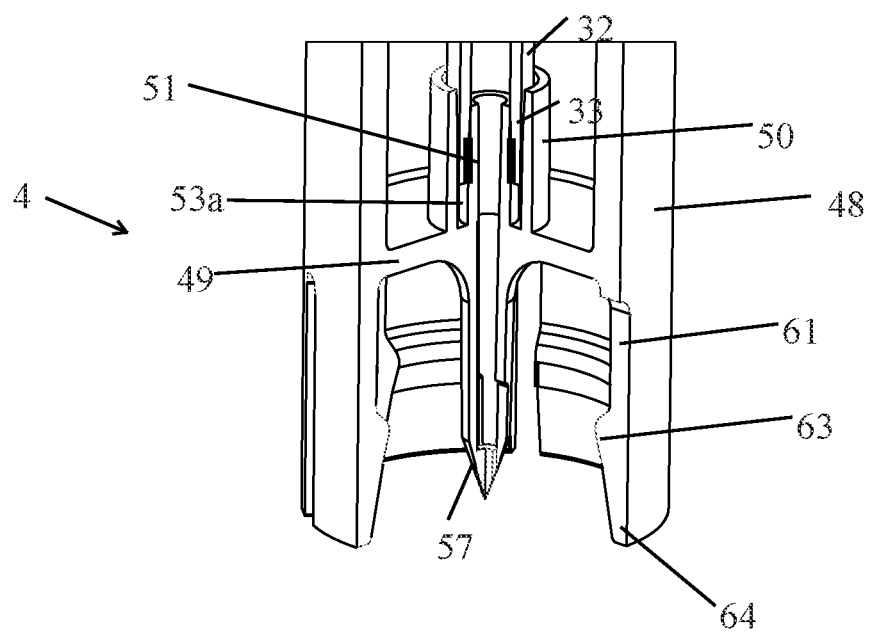
FIG. 2 shows details of coupling the components of the liquid pump dispenser of FIG. 1 in a schematic exploded view.
Figure 2:
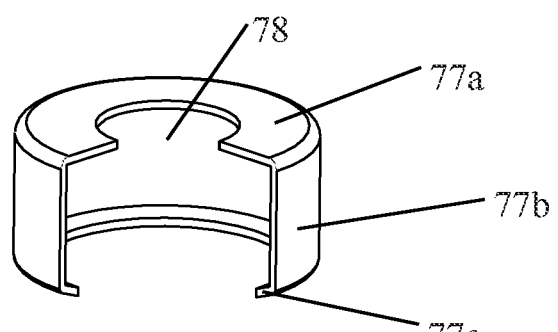
Figure 2:
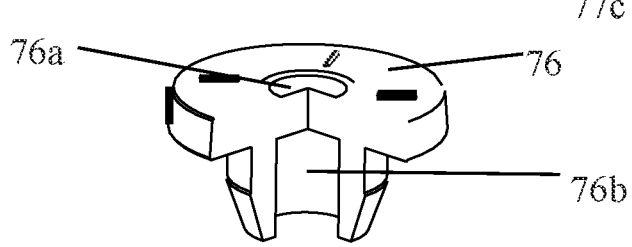
Figure 2:
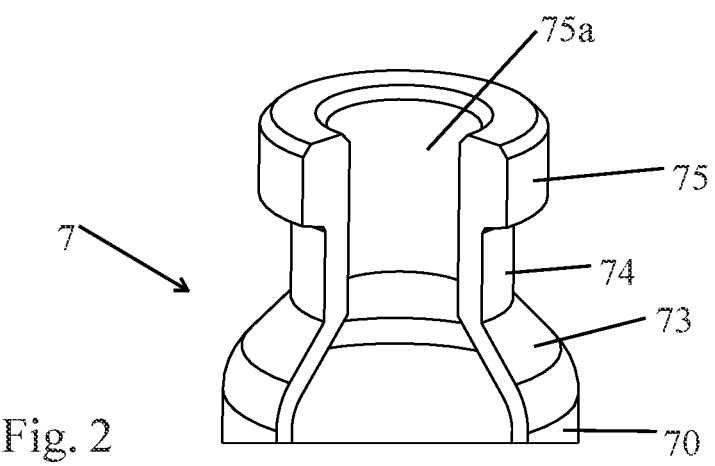

The general shape of a medical vial for use with a liquid pump dispenser according to the present invention is shown FIG. 2. The vial 7 that is preferably made of glass but may also be made of plastic material has a cylindrical vial body 70 with a closed bottom and a conical shoulder 73 that is followed by a constricted neck 74 and a wider rolled edge 75 that defines a filling opening 75a of the vial 7. The cylindrical shape of such a vial precisely defines a center line extending in an axial direction.

The filling opening 75a is sealed by an elastomeric stopper 76 that has a central piercing portion, to be pierced or punctured by the piercing mandrel 57 of the vial adapter 4, and a central channel 76b through which the piercing mandrel 57 extends into the inner volume of the vial 7 when the vial adapter 4 is locked to the front end of the vial 7 to establish a channel for the transfer of liquid out of the vial 7 via the vial adapter 4. In the center, the thickness of the stopper 76 is smallest. A cylindrical metal cap 77 is used to hold the stopper 76 in place at the front end of the vial 7. A bottom edge 77c of the metal cap 77 grips behind the bottom of the rolled edge 75 of the vial 7, to hold the stopper 76 in place when the cylindrical metal cap 77 is crimped over the rolled edge 75. A circular central opening 78 is defined in the upper surface 77a of the metal cap 77 and exposes the central piercing portion 76a of the stopper 76.

Figure 1:
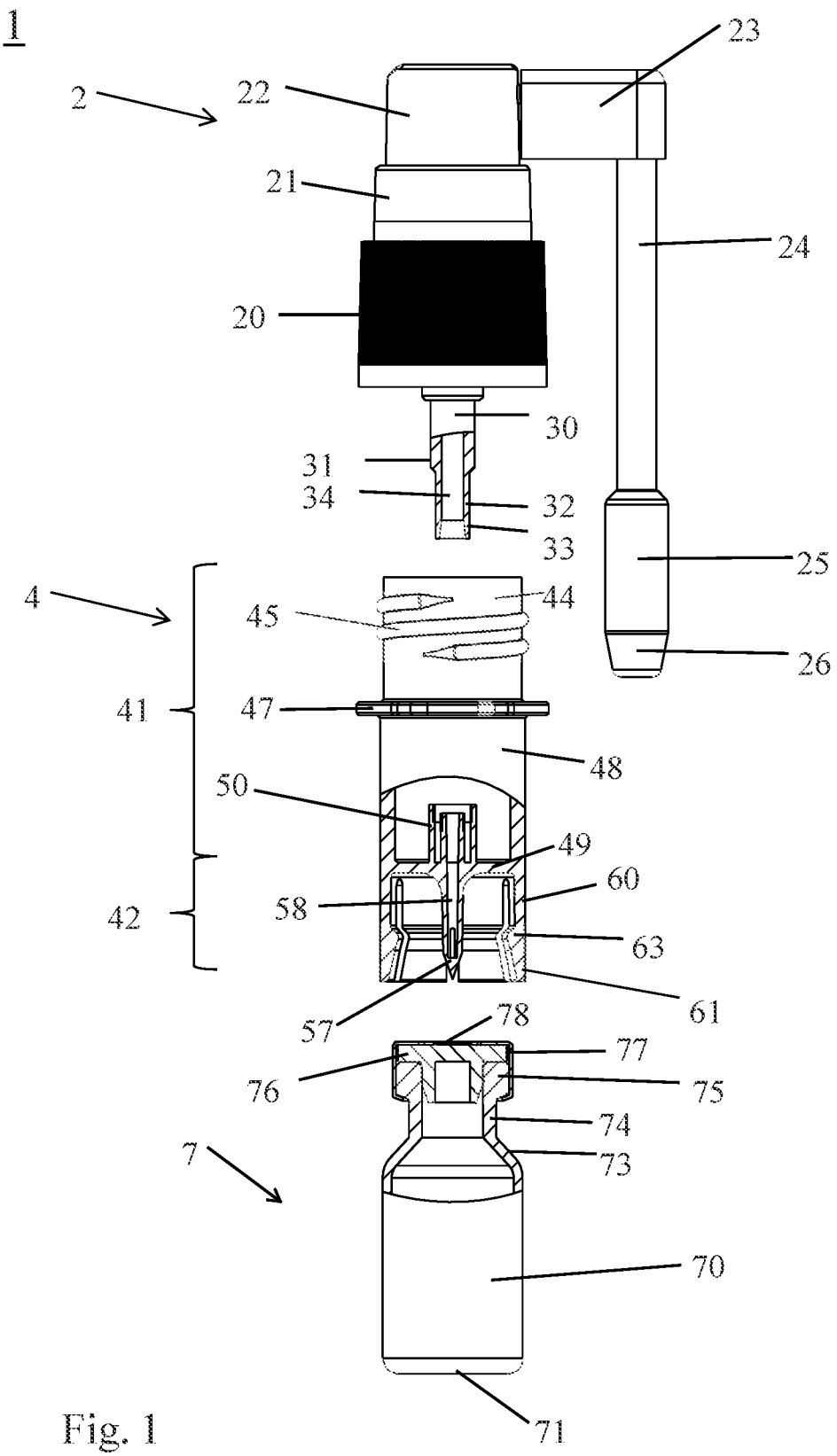
FIG. 1 shows a liquid pump dispenser according to a first embodiment of the present invention in a schematic exploded view.
Figure 4A:
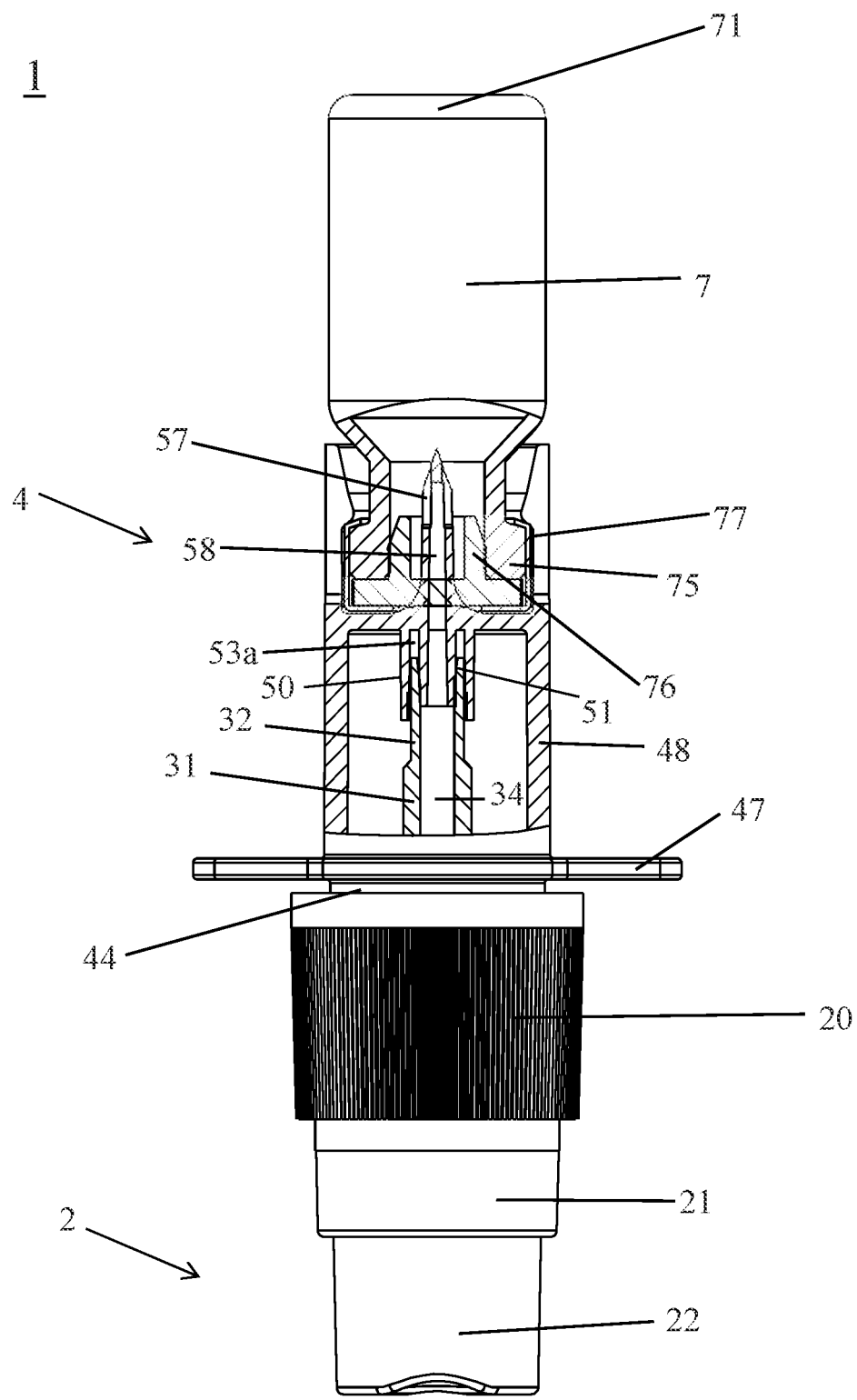
FIG. 4a shows a partial cross-section of a liquid pump dispenser according to the present invention when locked onto the front end of a vial and with the piercing mandrel of the vial adapter piercing a vial stopper.

FIG. 1 shows an example of a vial adapter 4 according to a first embodiment of the present invention for use with a pump dispenser unit 2. The vial adapter 4 is formed as a hollow tubular body 48 having a first end 44 and a second end 64 opposite to the first end 44. The hollow tubular body 48 comprises an upper coupling portion 40 for connecting the vial adapter 4 with the pump dispenser unit 2, a central main body 41 with a tube coupling structure 50 for coupling with a flexible inlet tube 30 (hereinafter 'connecting tube') of the pump dispenser unit 2, and a lower coupling portion 42 for connecting the vial adapter 4 with a vial 7. An outer thread 45 is provided on a cylindrical upper portion 44 of the tubular body 48 and serves as a first connecting means for connecting the vial adapter 4 with the pump dispenser unit 2 by threading the pump dispenser unit 2 on the cylindrical upper portion 44. A skirt or snapping ring 60 formed by a plurality of resilient legs 63 is provided at the bottom end of the tubular body 48. More specifically, the skirt 60 is formed by a plurality of resilient legs 61 disposed along a circumference of the tubular body 48 at the second end at equiangular spacing and spaced apart to each other via axial slots 62. The resilient legs 61 each comprise a protrusion 63 beveled inward into the lower half-space 56b of the tubular body 48. When the vial adapter 4 is locked on the front end or neck of a vial 7, as shown in FIG. 4a, the locking protrusions 63 grip behind the bottom of the rolled edge 75 of the vial 7 and the bottom edge of the metal cap 77. Thus, the resilient legs 61 serve as a second connecting means for connecting the vial adapter 4 with a vial 7 by latching.

A partition wall 49 extending perpendicular to an axial direction of the vial adapter 4 is provided inside the hollow tubular body 48 and separates the cavity 46 into a first (upper) half-space 56a and a second (lower) half-space 56b. A piercing mandrel 57 is disposed on the partition wall 49 in the second half-space 56b. The piercing mandrel 57 is configured for piercing the stopper 76 of the vial 7 for liquid transfer out of the vial and towards the pump dispenser 2. The piercing mandrel 57 forms a cannula 58 that is in fluid communication with the first half-space 56a of the tubular body 48 via a central hole in the center of the partition wall 49.

The resilient legs 61 of the skirt 60 can be flexed radially outwards. When the vial adapter 4 is pushed onto the front end of the vial 7, the bottom bevels of the protrusions 63 will finally get in contact with the outer perimeter of the metal cap 77 crimped onto the front end of the vial 7 and slide along the outer edge of the metal cap 77, and thus the resilient legs 61 start spreading apart. When the vial adapter 4 is pushed further onto the front end of the vial 7, the resilient legs 61 will continue to be spread apart and finally the piercing mandrel 57 will start piercing or puncturing the elastomeric stopper 76 sealing the opening at the front end of the vial 7. When the vial adapter 4 is pushed further onto the front end of the vial 7, finally the protrusions 63 will grip behind the bottom edge of the metal cap 77 and the piercing mandrel 57 will have fully penetrated or punctured the vial stopper 76, thus enabling a liquid transfer out of the vial 7 in the transfer position shown in FIG. 4a. As can be concluded from FIGS. 4a and 2, in the transfer position the piercing mandrel 57 extends through the piercing portion 76a and central channel 76b of the stopper 76 into the inner volume of the vial 7. The piercing mandrel 57 does not extend up to the bottom 71 of the vial 7, but rather extends only a relatively short distance into the inner volume of the vial 7. For establishing the liquid transfer, it may be sufficient, if the piercing mandrel 57 extends up to the neck 74 or shoulder 73 into the inner volume of the vial 7. The liquid pump dispenser 1 according to the present invention will thus be used in an upside-down orientation of the vial 7, as shown e.g., in FIG. 4a, where the liquid in the vial 7 flows to the piercing mandrel 57 automatically by gravity.

Figure 3A:
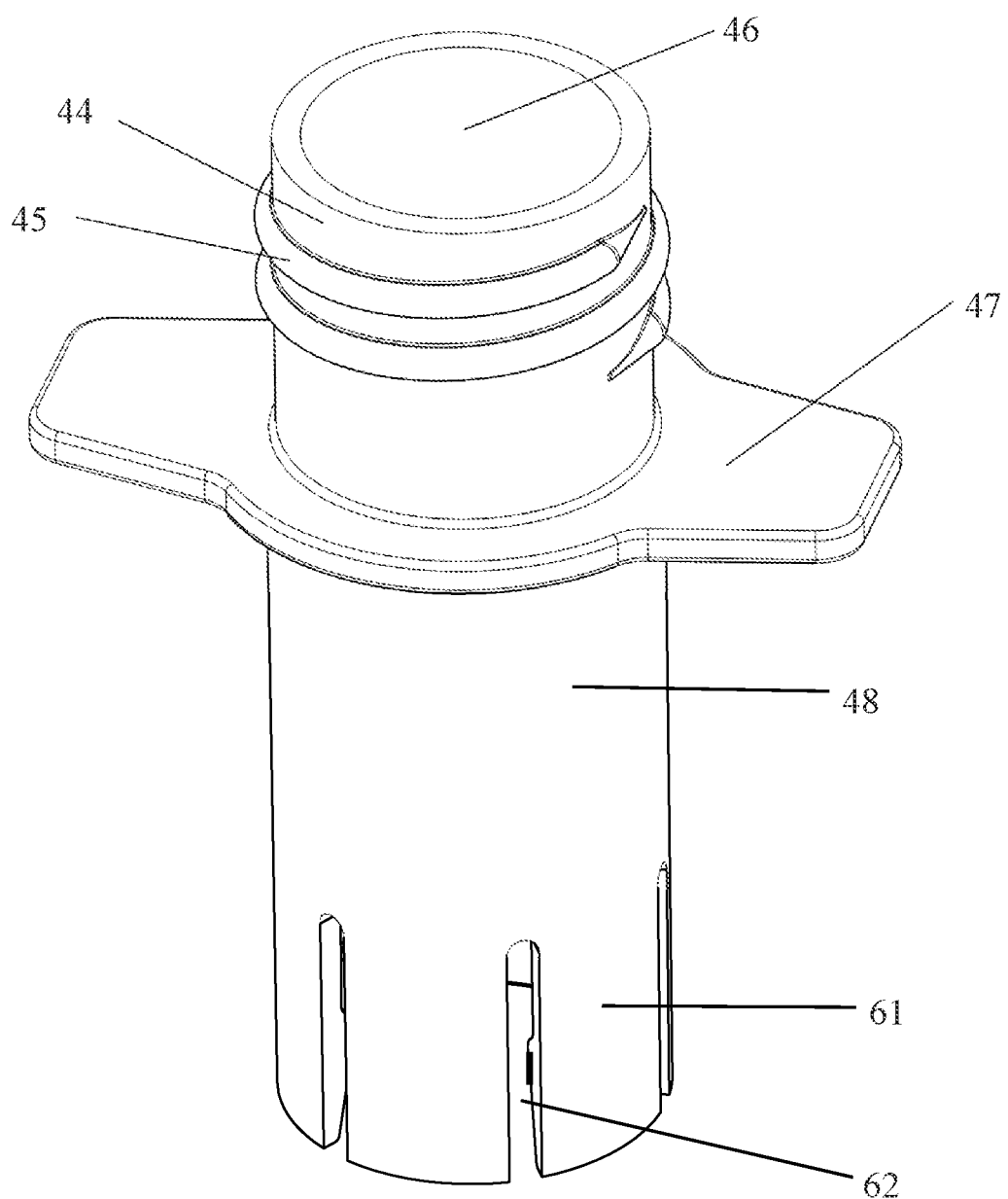
FIGS. 3a to 3e show a vial adapter according to a first embodiment of the present invention in a perspective top and bottom view, in a plan view and bottom view and in a side-view.
Figure 3B:
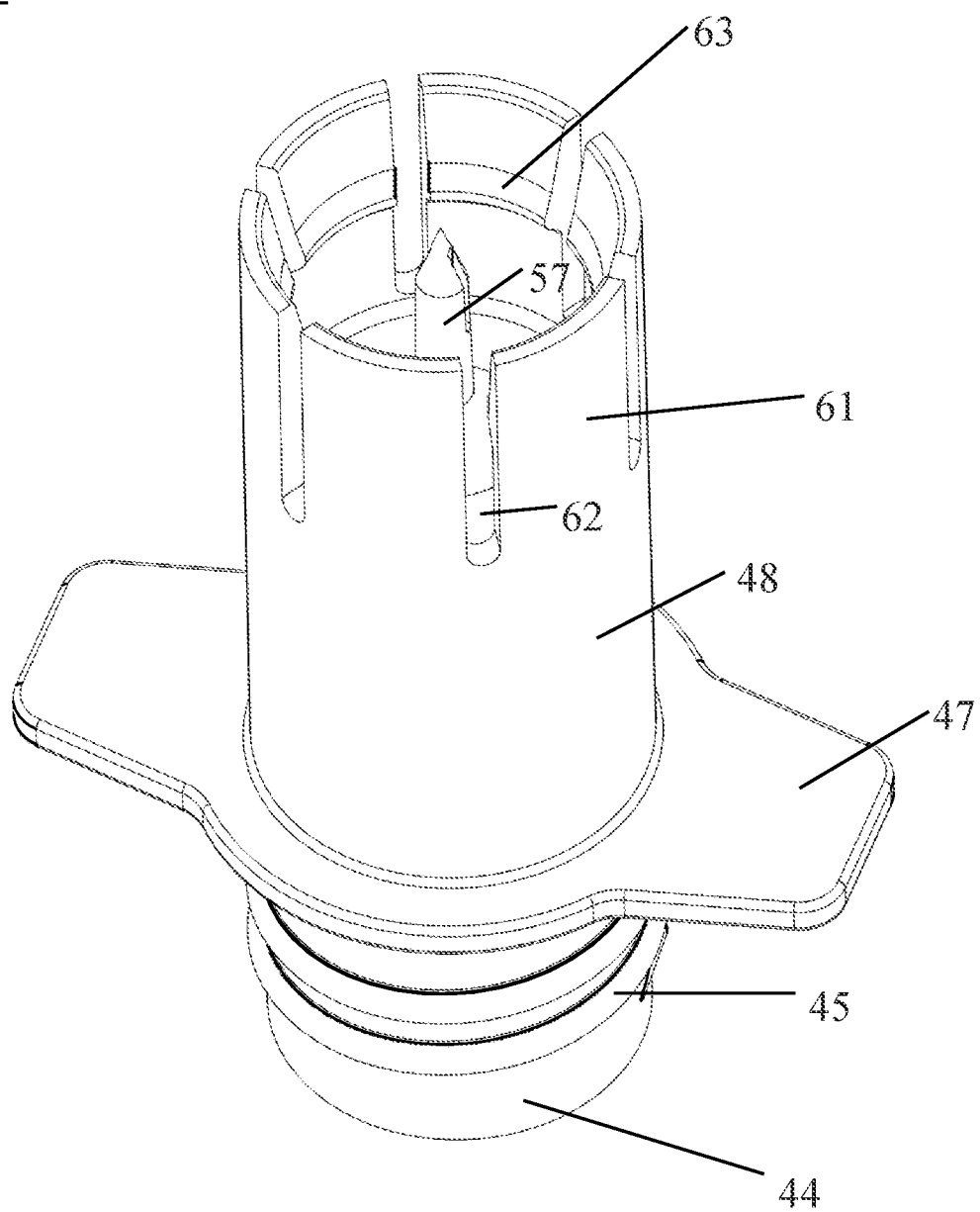
Figure 3C:
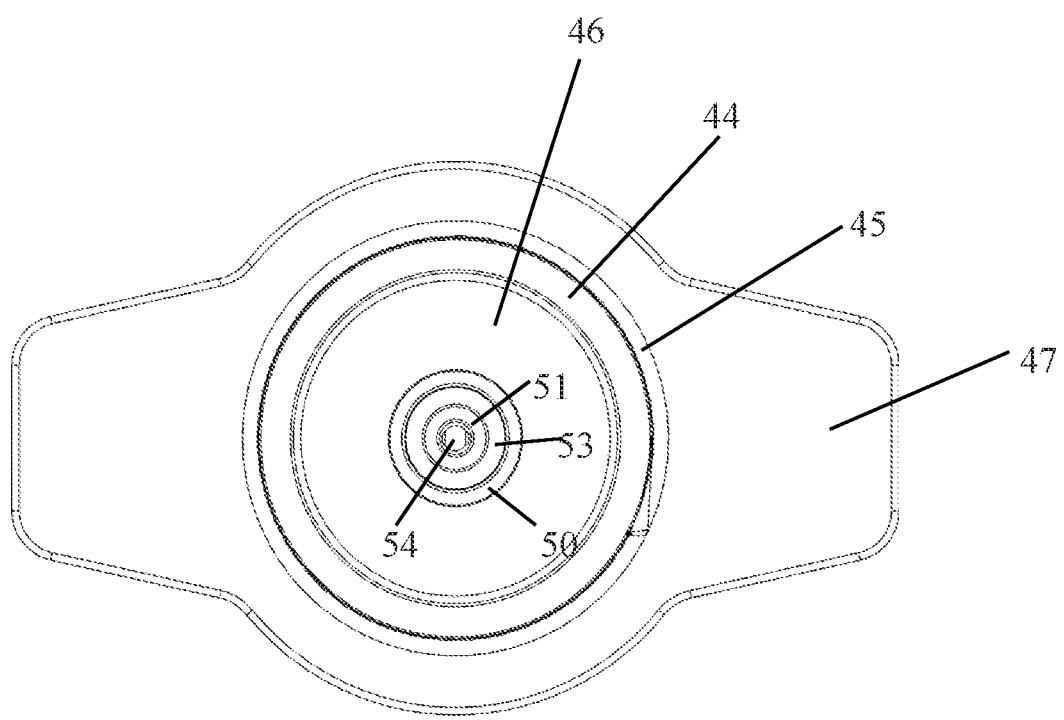
Figure 3D:
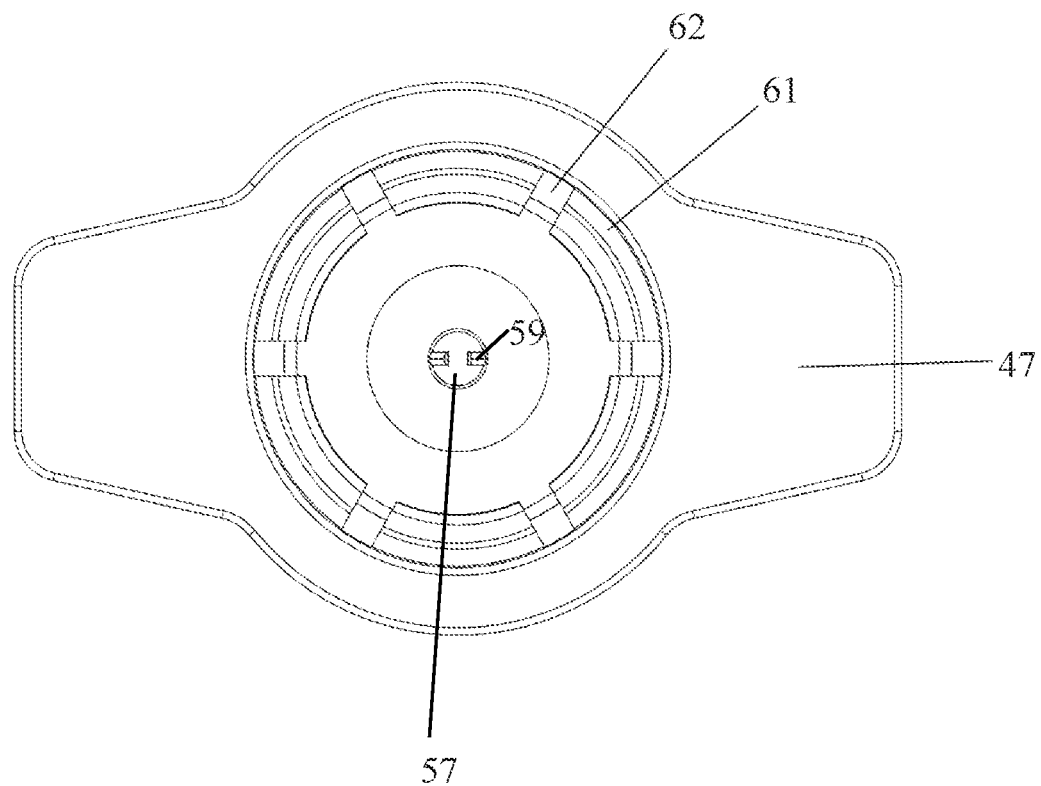
Figure 3E:
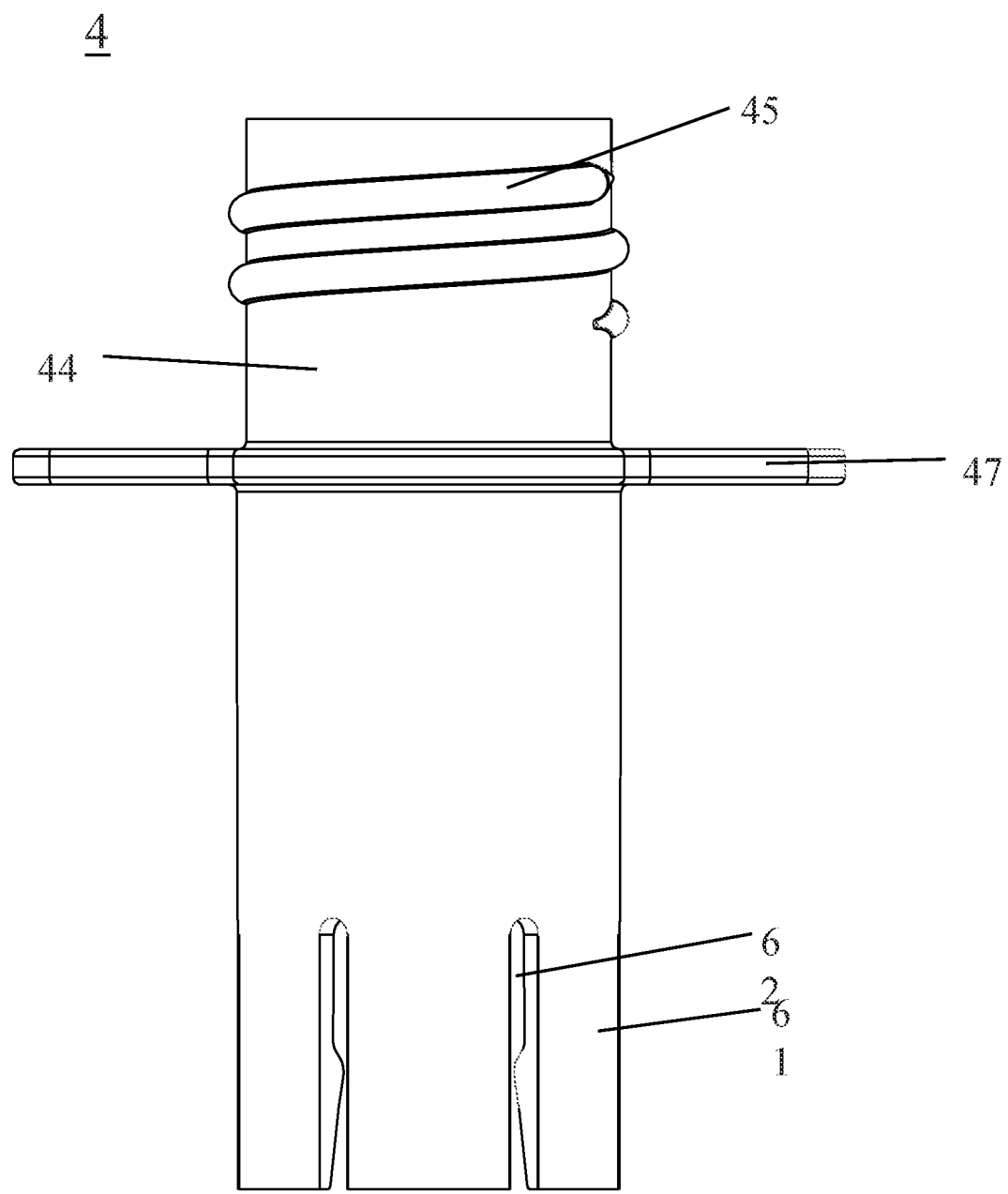
Figure 3F:
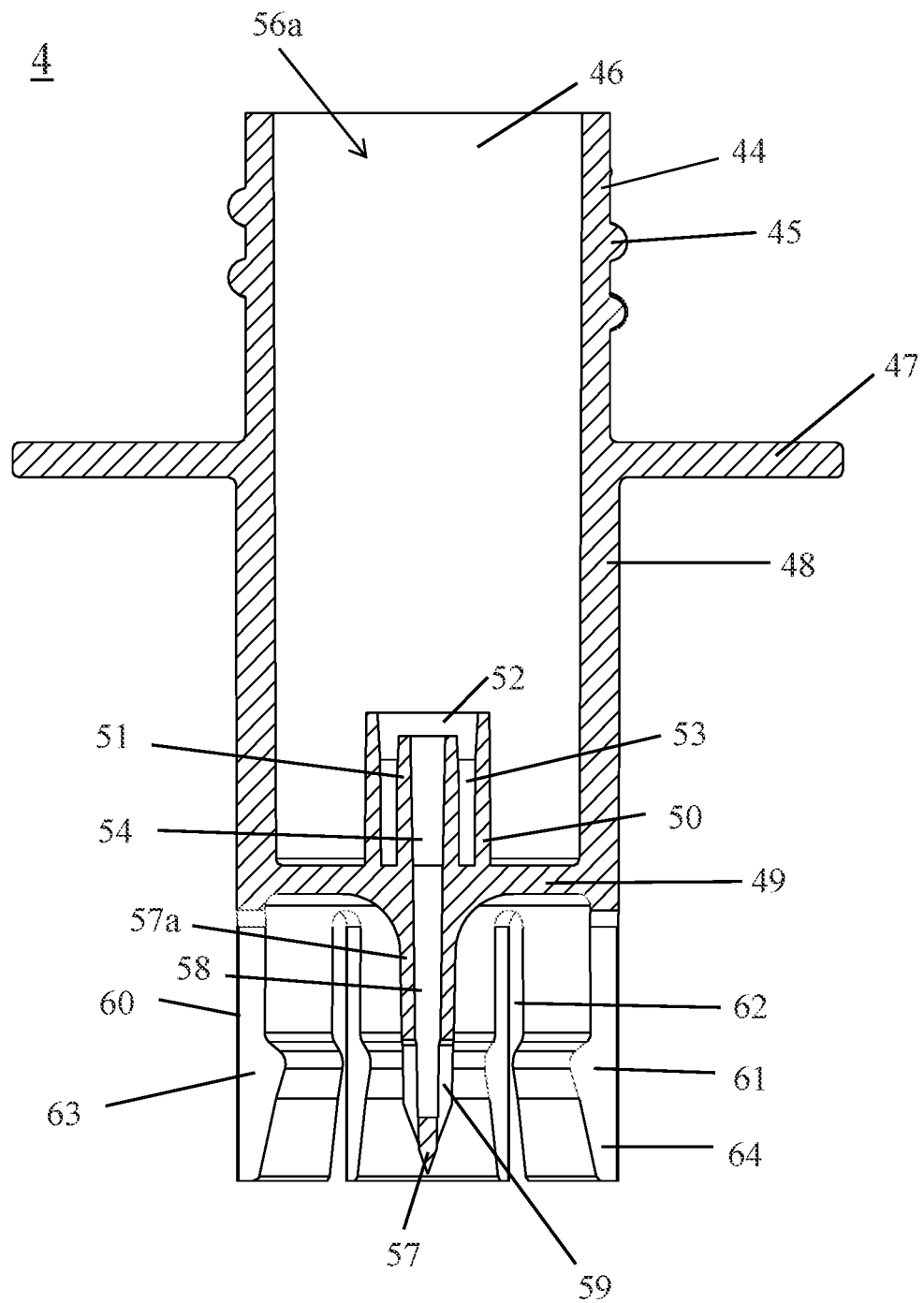
FIG. 3f shows the vial adapter of FIGS. 3a to 3e in a schematic cross-section.

As shown in FIGS. 1 and 3f, the piercing mandrel 57 does not protrude beyond the bottom end 64 of the skirt 60 of the vial adapter 4. The vial adapter 4 can thus be packaged safely, e.g., in a blister pack, without the risk of piercing a plastic sealing foil of the blister pack. More specifically, the height of the front end of the piercing mandrel 57 above the bottom end 64 of the vial adapter 4 (or above a plane spanned by the annular bottom end 64 of the vial adapter 4) is preferably in the range of 0.4 to 2.0 mm, more preferably in the range of 0.4 to 1.0 mm.

As can be concluded from FIGS. 1 and 3f, a height, where an inner diameter of a circle formed by the beveled protrusions 63 corresponds to an outer diameter of the metal cap 77 of the vial 7, corresponds to or is less than the height of a front end of the piercing mandrel 57 above the bottom of the skirt 60 of the vial adapter 4. More specifically, the height of the front end of the piercing mandrel 57 above the level, where the inner diameter of a circle formed by the beveled protrusions 63 corresponds to the outer diameter of the metal cap 77 provided on a front end of the vial 7, is preferably in the range of 0.4 to 2.0 mm, more preferably in the range of 0.4 to 1.0 mm.

This ensures that the bottom skirt 60 of the vial adapter 4 will first be centered on the metal cap 77 of the vial, as the bottom ends of the beveled protrusions 63 first get in contact with the outer perimeter of the metal cap 77 when the vial adapter 4 is pushed onto the front end of the vial 7. After this auto-centering of the vial adapter 4, the resilient legs 61 begin being spread apart as the vial adapter 4 is pushed further onto the vial 7, as the bottom ends of the beveled protrusions 63 start sliding along the outer perimeter of the metal cap 77 when the vial adapter 4 is pushed further onto the front end of the vial 7. Only then will the piercing mandrel 57 start to pierce the stopper 76 of the vial 7. Hence, the afore-mentioned spatial relationship between the front end of the piercing mandrel 57 and the bottom end 64 of the skirt 60 of the vial adapter 4 ensures that the piercing mandrel 57 automatically pierces or punctures the stopper 76 of the vial at its center. Hence, the piercing mandrel 57 will not (or not significantly) be flexed sideward when it pierces or punctures the vial stopper 76 so that it may be sufficient for a liquid transfer if the piercing mandrel 57 just extends a relative short distance into the channel 76b of the stopper and into the inner volume of the vial 1. In other words, the piercing mandrel 57 of the vial adapter 4 according to the present invention may be relatively short.

As shown in FIG. 3f, a tube coupling structure is provided on the upper surface of the partition wall 49 and protrudes into the upper half-space 56a of the tubular body 48. The tube coupling structure is formed at least by an outer cylindrical wall 50 forming a cylindrical cavity of a width corresponding to an outer diameter of the connecting tube of the pump dispenser unit to be accommodated therein.

As shown in FIG. 3d, the tube coupling structure may additionally comprise an inner cylindrical wall 51 concentric to the outer cylindrical wall 50. The cylindrical walls 50, 51 each protrude perpendicular from the partition wall 49 into the first half-space 56a. A cylindrical cavity 53 is formed between the two cylindrical walls 50, 51. The cavity 53 serves for accommodating a front end 33 of the connecting tube 30 in a fluid-tight manner, as shown in FIG. 2. The width of this cylindrical cavity 53 corresponds to the thickness of the front end 33 of the connecting tube 30, for fluid-tight engagement.

As shown in FIG. 3f, an upper edge 52 on the inner surface of the outer cylindrical wall 50 may be beveled inward so that the bottom end 32 of the connecting tube 30 will be guided smoothly into the cylindrical cavity 53, when the pump dispenser unit 2 is threaded on the cylindrical portion 44 of the vial adapter 4.

The width of the cylindrical cavity 53 may correspond to a wall thickness of the bottom end 32 of the connecting tube 30. Moreover, a height of the cylindrical cavity 53 may be dimensioned such that a free space 53a remains between the front end 33 of the connecting tube 30 and an upper surface of the partition wall 49, when the pump dispenser unit 2 is threaded on the vial adapter 4, as shown in FIG. 2. Thus, a compression or crushing of the front end 33 of the connecting tube 30 is reliably prevented, which further assists to accommodate the front end 33 of the connecting tube 30 in the cylindrical cavity 53 in a fluid-tight manner.

As shown in FIG. 1, the wall thickness of the front end 33 of the connecting tube 30 may be smaller in the lower portion 32 of the inlet tube 30 as compared to the upper portion 31, so that the lower portion 32 may be a little more flexible and the front end 33 of the connecting tube 30 may slide smoothly into the cylindrical cavity 53, when the pump dispenser unit 2 is put and threaded on the cylindrical portion 44 of the vial adapter 4.

As shown in FIG. 1, the inner surface of the front end 33 of the connecting tube 30 may be beveled, to further assist guiding the front end of the connecting tube 30 into the cylindrical cavity 53 when the pump dispenser unit 2 is put and threaded on the cylindrical portion 44 of the vial adapter 4.

To ensure that the front end 33 of the connecting tube 30 is first captured and centered by the outer cylindrical wall 50 before it slides into the cylindrical cavity 53 formed between the two cylindrical walls 50 and 51, the height of the outer cylindrical wall 50 above the partition wall 49 may be larger than the height of the inner cylindrical wall 51 above the partition wall 49.

Generally, the connecting tube 30 may be integrally formed with the piston housing 310 of the pump dispenser unit 2, as long it is flexible enough, which can be accomplished e.g., by use of 2K-injection molding techniques. More preferably, however, the connecting tube 30 will be a separate member not integrally formed with the piston housing 310 of the pump dispenser unit 2.

According to an alternative embodiment, the connecting tube may also be integrally formed with the partition wall 49 and the cylindrical wall 50 of the vial adapter and accommodated accordingly in a tube coupling structure provided on the piston housing 310 of the pump dispenser unit 2.

According to the present invention, the connecting tube 30 is made of a flexible plastic material, e.g., of a soft rubber or polymeric plastic material. The connecting tube 30 may thus serve to compensate any misalignment or relative displacement between the vial adapter 4 and pump dispenser unit 2 during assembly or use. Because the connecting tube 30 is accommodated in a fluid-tight manner in the tube coupling structures, a reliable operation of the liquid pump dispenser 1 without leakage can be accomplished. Moreover, the connecting tube 30 may also assist in absorbing any axial stress or load acting on the vial adapter 4 and/or pump dispenser unit 2 during assembly or later use, particularly when the push button 22 of the pump dispenser unit 2 is pushed.

As shown in FIGS. 3a to 3f, a finger-rest 47 may be provided on and formed integral with the outer surface of the hollow tubular body 48. The finger-rest 47 protrudes outward in radial direction from the outer surface of the hollow tubular body 48. The finger-rest comprises two wing-shaped protrusions 47 provided on diametral opposite sides on the outer surface of the hollow tubular body 48, which tends to cause a slight displacement of the pump dispenser unit 2 relative to the vial adapter 4.

The pump dispenser unit 2 may be a standard dispenser pump available on the market, and could be a ball-type dispenser pump. Extensive experiments of the applicant showed, however, that a reliable operation without leakage and dripping at an outlet nozzle cannot be ensured for ball-type dispenser pumps, if operated in an upside-down orientation of the vial. Therefore, according to the present invention the pump dispenser unit 2 is a ball-less dispenser pump of the piston-type, including a central pump housing, which defines a piston chamber, in which a piston is movably supported. The experiments of the applicant showed that a piston-type pump dispenser unit can be operated reliably in an upside-down (inverted) orientation of the medical vial, without the problems of leakage and dripping at an outlet nozzle, and moreover enables a precise and repeatable dosage of the liquid pumped out of the medical vial.

For medical applications, the pump dispenser unit 2 may be stored in a sterile packaging, e.g., a sterile blister pack. More preferably, the pump dispenser unit 2 is stored in a sterile packaging together with the vial adapter 4, preferably already connected with each other, e.g., by threading. Preferably, the total length of the tube 24 of the pump dispenser unit 2, if provided, may be such that it does not extend beyond the bottom edge of the vial adapter 4, when the pump dispenser unit 2 is connected to the vial adapter 4. For this purpose, it may be helpful if the tube 24 is a telescopic tube 24. Thus, the liquid pump dispenser consisting of the pump dispenser unit 2 connected to the vial adapter 4 is of generally cylindrical shape and can thus be packaged easily, particularly in a blister pack.

The vial 7 may also be provided under sterile conditions, e.g., packaged in a sterile blister pack. For establishing the liquid pump dispenser 1 shown in FIGS. 4a and 4b, first the packaging of the unit consisting of the pump dispenser unit 2 connected to the vial adapter 4 and the packaging storing the vial 7 is opened. Then, the vial adapter 4 is pushed and locked on the front end of the vial 7, as outlined above.

As the unit consisting of the pump dispenser unit 2 connected to the vial adapter 4 and the vial 7 has been stored preferably under sterile conditions, the liquid pump dispenser 1 of FIG. 4a is ready for use.

If the vial 7 should not be stored under sterile conditions, it might be necessary to disinfect only the central exposed portion 76a of the vial stopper 76, e.g., by means of a disinfecting swab, before coupling the vial adapter 4 with the vial 7. The liquid pump dispenser 1 may thus be obtained quickly, reliably and under sterile conditions.

Figure 4B:
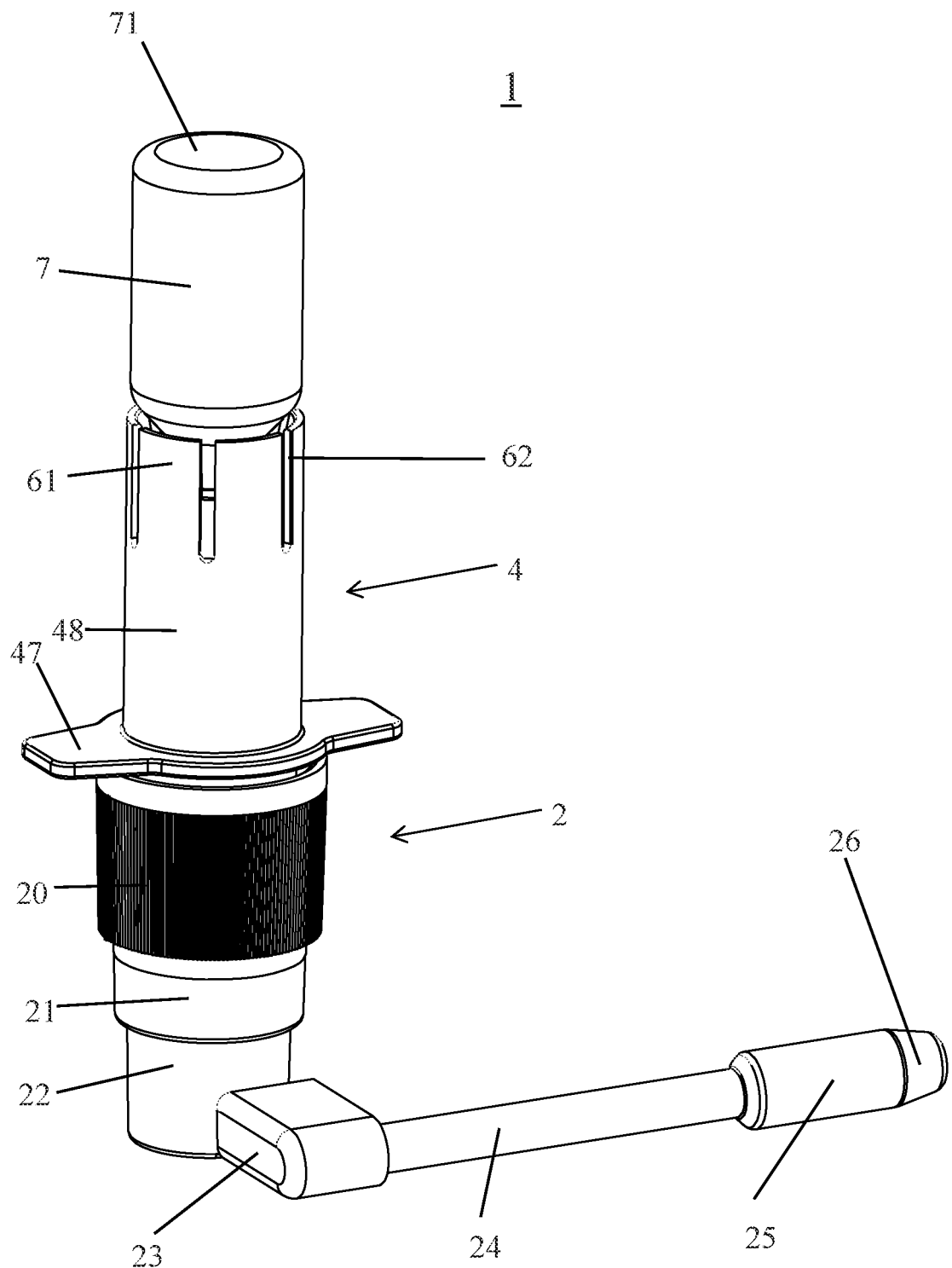
FIG. 4b is a perspective view of the liquid pump dispenser of FIG. 4b.

As the piercing mandrel 57 extends only a short distance into the inner volume of the vial 7, the vial 7 needs to be held upside down in use, as shown in FIGS. 4a and 4b. I.e., in the use-position, the vial 7 forms the top portion of the liquid pump dispenser 1 so that liquid can be supplied to the pump dispenser unit 2 even if the vial 7 is nearly empty. For use, the liquid pump dispenser 1 is held upside-down and the user's forefinger and middle finger rest against the finger rest 47, while the operating button 22 of the pump dispenser unit 2 can be actuated by the user's thumb to push it towards the main body 21, so that liquid is transferred via the piercing mandrel 57 and the connecting tube 30 towards the pump dispenser unit 2, from where it is pumped via the tube 24 towards the outlet 26, where the contents of the vial 7 may be sprayed as a fine mist by means of a spraying nozzle. The liquid pump dispenser 1 can be operated in a sanitary, convenient and easy fashion without leakage.

As shown in FIG. 4*b*, the tube 24 may be pivoted in a direction perpendicular to the axial direction of the liquid pump dispenser 1, so that the contents of the vial 7 may be sprayed as a fine mist deep into the throat of a person, e.g., for treatment of a tonsillitis.

The liquid pump dispenser 1 may be used to spray any type of medical liquid. The liquid may be in particular a medical drug or a vaccine.

The liquid pump dispenser 1 may be delivered to customers packaged in a packaging. FIGS. 5*a* and 5*b* show an example of such a packaging 10. In this example, the packaging 10 is formed by a cylindrical main body 100 formed by a cylindrical, tapered side-wall, which is closed at its first end by a closed, planar bottom 101 and which includes an annular, flat flange 102 at its open second end opposite to the first end. A plastic packaging foil 104 may be adhesively bonded to the flange 102, ready to be torn-off by grasping a flap 105 provided at a perimeter of the sealing foil 104.

The main body 100 may be formed by deep-drawing or thermo-forming a thin plastic sheet but may also be formed by plastic injection-molding or other techniques. As an alternative, the main body 100 may also be made of paper or cardboard. A thin film of plastic or bioplastic may be arranged on inner surfaces of the main body 100 to enable even the storage of the liquid pump dispenser 1 under sterile conditions. DE 102011122211 A1 discloses an example of such a compound packaging material including a substrate made of paper or cardboard that is coated by a thin film of plastic or bioplastic, and the whole contents of DE 102011122211 A1 is hereby incorporated by reference. Of course, the main body 100 may also be made simply of paper, cardboard or any other material without such a thin film, e.g., if it should not be necessary to package the liquid pump dispenser 1 under sterile conditions.

The packaging foil 104 shown in FIG. 5*a* may also be a Tyvek®-foil or similar foil to enable a sterilization of the content and whole inner volume of the packaging 1, if required, by a vapor or steam flowing into the inner volume of the packaging 10 via the packaging foil 104.

After removal of the packaging foil 104 from the flange 102 of the main body 100, the liquid pump dispenser 1 can be removed out of the packaging 10, as shown in FIG. 5*b*. The vial adapter 4 may then be pushed onto the front end of a vial (not shown) for coupling, to enable the transfer of liquid out of the vial via the pump dispenser 2 and the outlet 26, as outlined above.

Of course, a liquid pump dispenser 1 and/or a vial adapter 4 as outlined above may also be stored/packaged in any other kind of packaging, such a pouch or container.

Figure 5A:
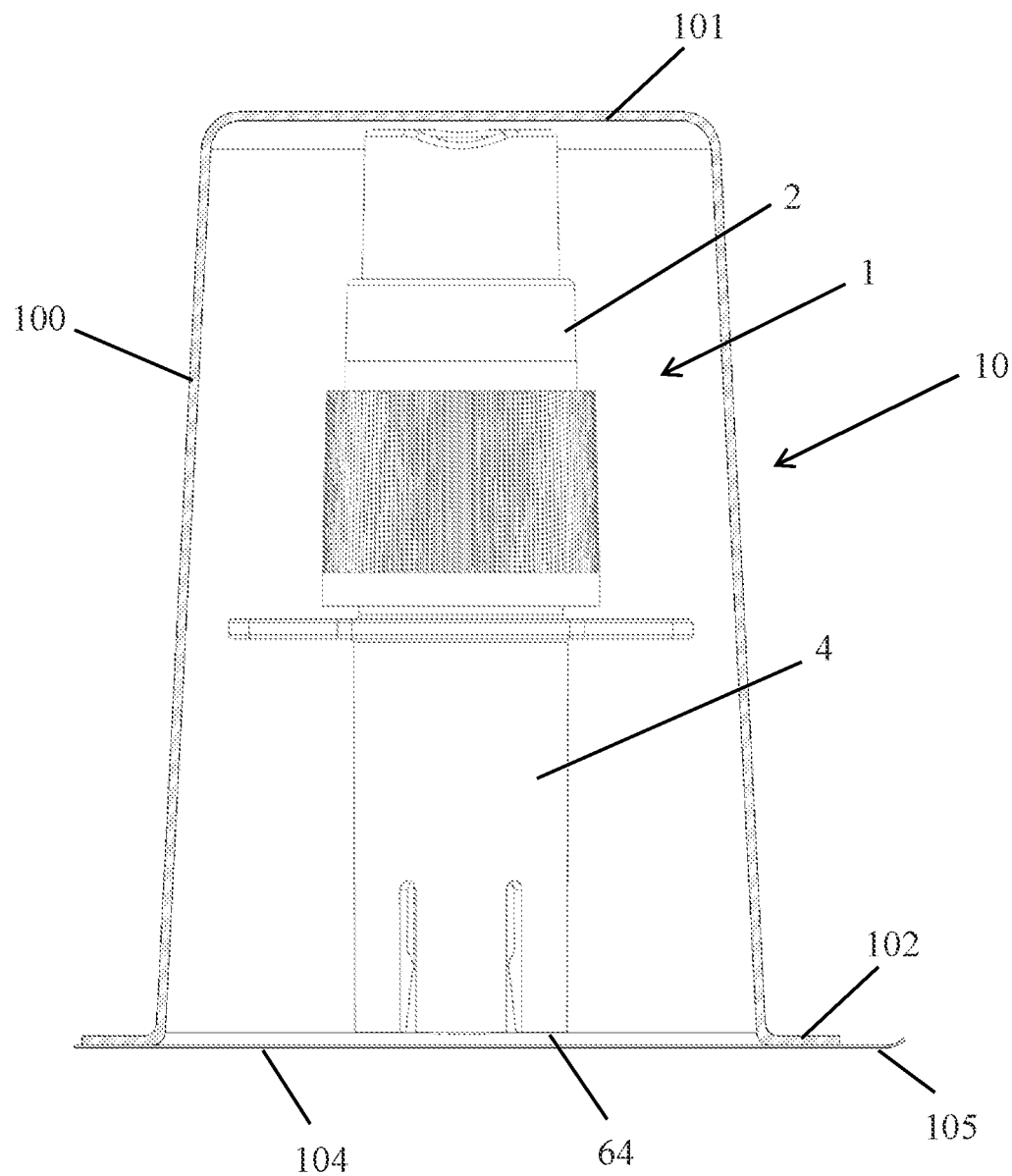
FIG. 5a shows a packaging unit for packaging a liquid pump dispenser according to the present invention in a schematic partial cross-section.
Figure 5B:
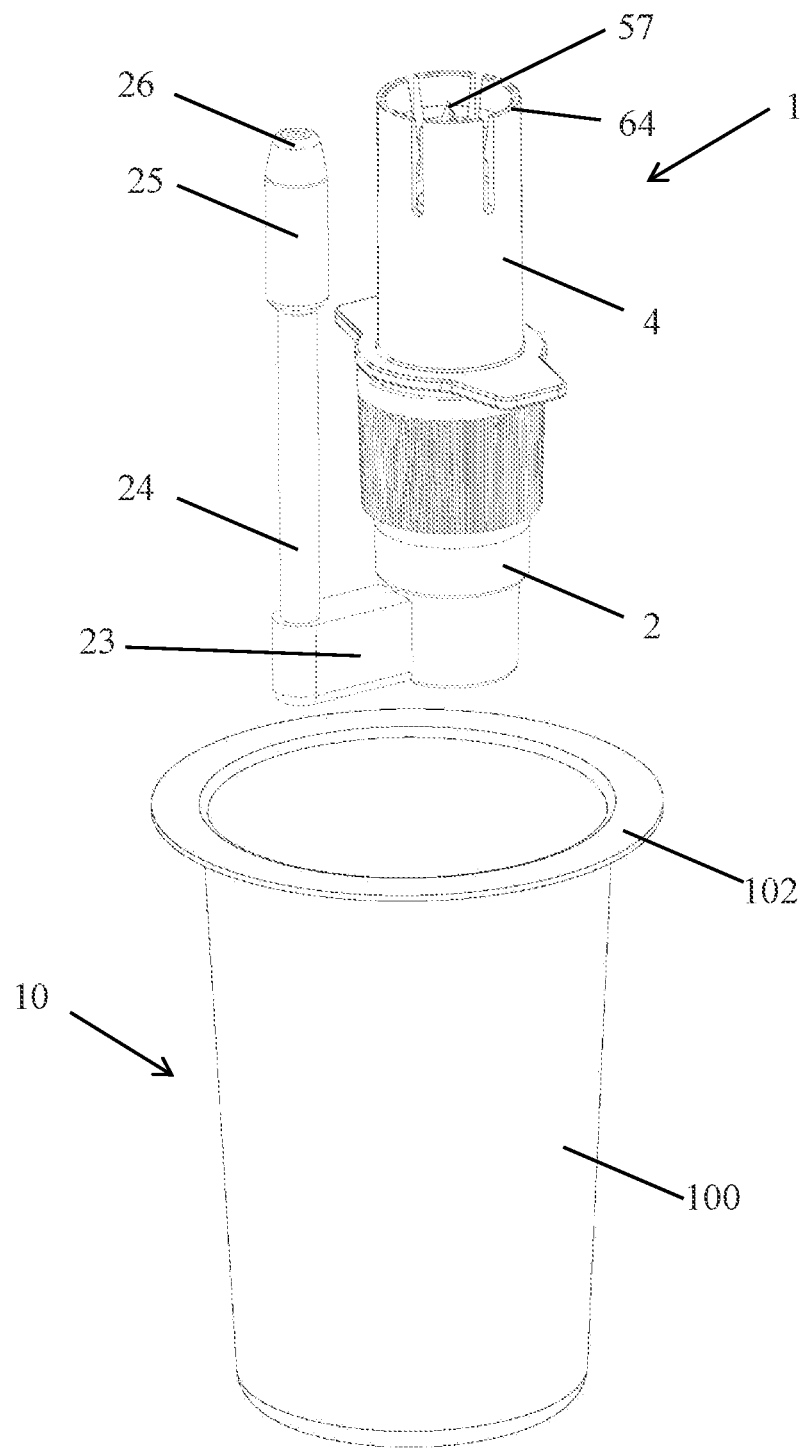
FIG. 5b shows the packaging unit of FIG. 5a in an exploded view with the liquid pump dispenser removed from the main body of the packaging unit after removal of a sealing foil.

As the piercing mandrel of the vial adapter does not protrude beyond the bottom end 64 of the vial adapter 4, the pump dispenser unit 2 and/or a vial adapter 4 can be packaged easily and reliably in many different kinds of packaging, including a packaging with a sealing foil of the type shown in FIGS. 5a and 5b. In such a case the piercing mandrel will not deteriorate the packaging, e.g., by piercing or damaging the sealing foil 104 shown in FIG. 5a.

Figure 6A:
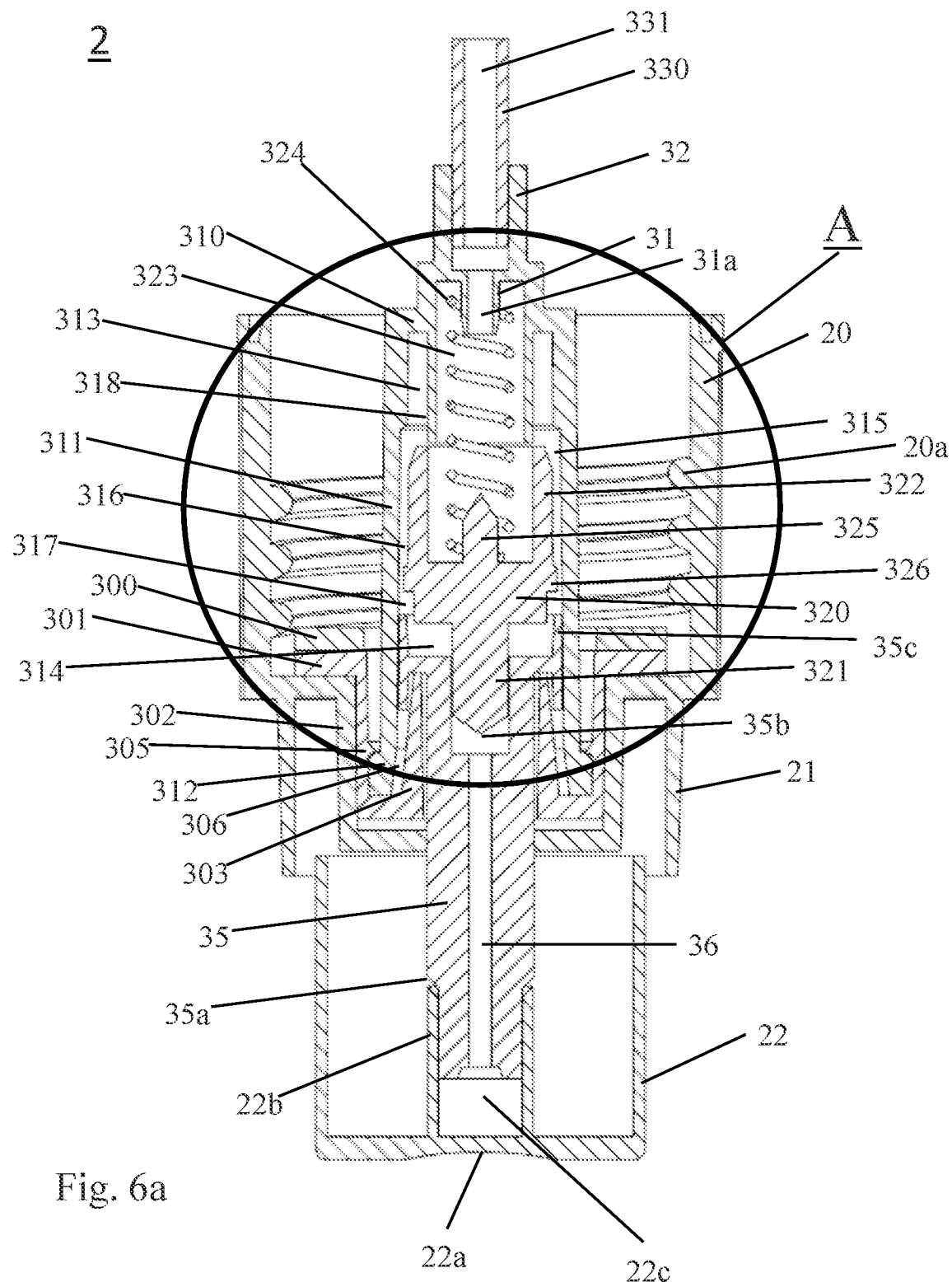
FIG. 6a shows the details of a piston pump of a second embodiment of a pump dispenser unit according to the present invention.
Figure 6B:
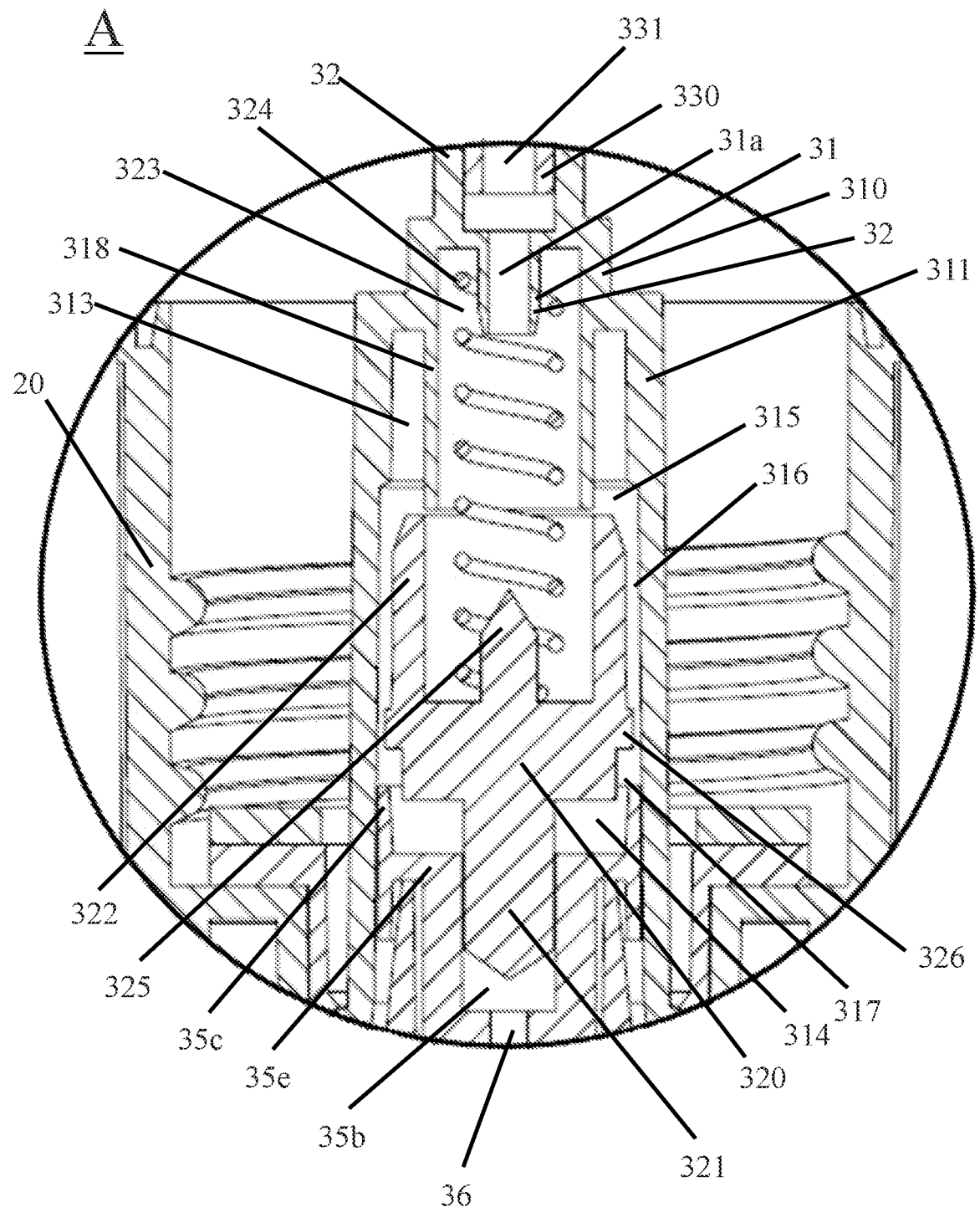
FIG. 6b shows detail A of FIG. 6a on an enlarged scale.

With reference to FIGS. 6a and 6b details of a piston-type dispenser pump of a preferred second embodiment according to the present invention will be described. A hollow cylindrical member 310, which has a cylindrical side-wall 311 that forms a piston housing, is held by a holding ring 300 at the bottom of collar 20. More specifically, the holding ring 300 pushes an annular holding arm 301 against the bottom of the collar 20. The annular holding arm 301 is followed by a cylindrical outer side-wall 302 and a cylindrical inner side-wall 303, which form a cylindrical cavity 306 with a latching protrusion 305 protruding into the cylindrical cavity 306. The latching protrusion 305 latches a thickened latching portion 312 provided at the bottom end of the side-wall 311 of the cylindrical member 310. The upper portion 313 of the piston chamber formed inside the cylindrical member 310 is separated by an upright cylindrical partition wall 318 from a cylindrical space 323, which is in fluid communication with the inlet 31a and the duct of the flexible connecting tube 330.

Figure 8A:
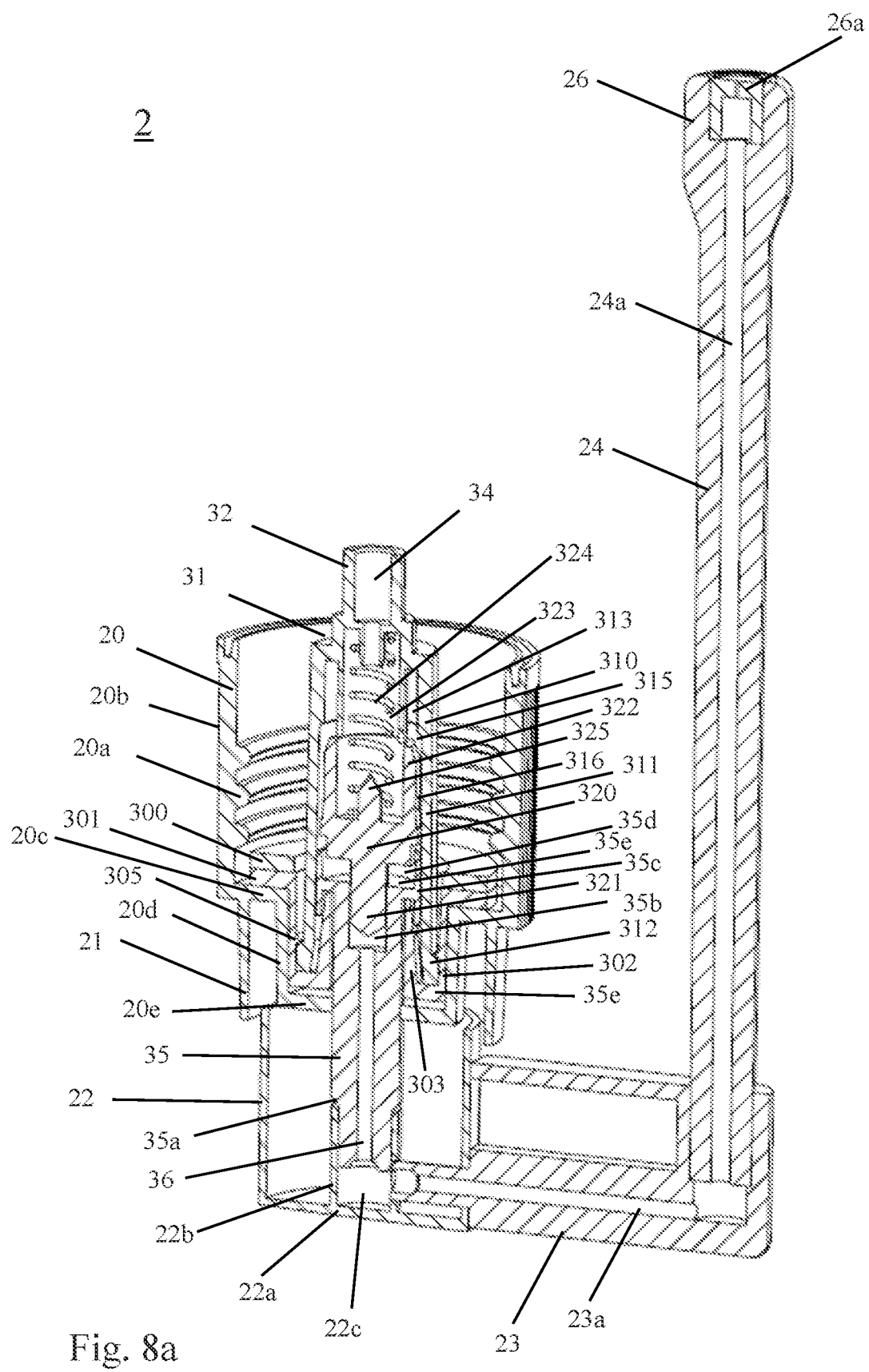
FIG. 8a is a cross-sectional view of a pump dispenser unit of a third embodiment according to the present invention.

A cylindrical piston 35 closes the bottom end of the piston chamber and is supported with a stepped portion 35a on an upright supporting cylinder 22b formed on the inner end surface or bottom 22a of the operating button 22. Pushing the operating button 22 towards the collar 20 will move the piston 35 in the piston chamber 314 towards inlet 31a. A central channel 36 is formed inside the piston 35, which is in fluid communication with a transfer chamber 22c and outlet 26 of the pump dispenser unit 2 (see FIG. 8a), and at the upper end of the piston 35 a widened central bore 35b is provided in which a cylindrical bottom end (supporting member) 321 of a sealing member 320 is supported, so that the sealing member 320 is moved together with the piston 35, the the operating button 22 is actuated.

In the bottom-most position of the piston 35 shown in FIGS. 6a and 6b, the upper end of the cylindrical upper sealing member 322 is disposed slightly below the front end of the partition wall 318, so that an upper transfer channel 315 is formed at this position. The cylindrical upper sealing member 322 is guided in a cylindrical guiding slot 313 at the upper end of the piston chamber 314. A resilient resetting force, for resetting the piston 35 and sealing member 320 to the home position shown in FIGS. 6a and 6b, is provided by a spring 324, which is supported on the cylindrical spring supporting member 325 and biased against the upper portion 31 of the central cylinder 310. As an alternative, the spring 324 could also be disposed on the bottom 22a of the operating button 22 and biased against the bottom end of the collar 20.

Once the upper end of the cylindrical upper sealing member 322 is pushed beyond the front end of the cylindrical partition wall 318, the piston chamber 314 will be sealed against the pump inlet chamber 323. The dosage to be ejected by the pump dispenser unit 2 will thus be defined precisely by the volume of piston chamber 314.

Figure 7C:
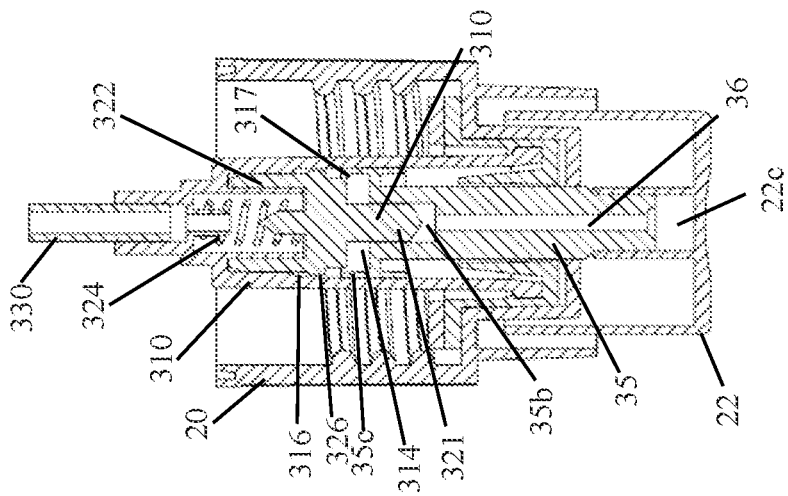
FIGS. 7a to 7c show the pump dispenser unit of the second embodiment at three different positions of the operating button during use.
Figure 7B:
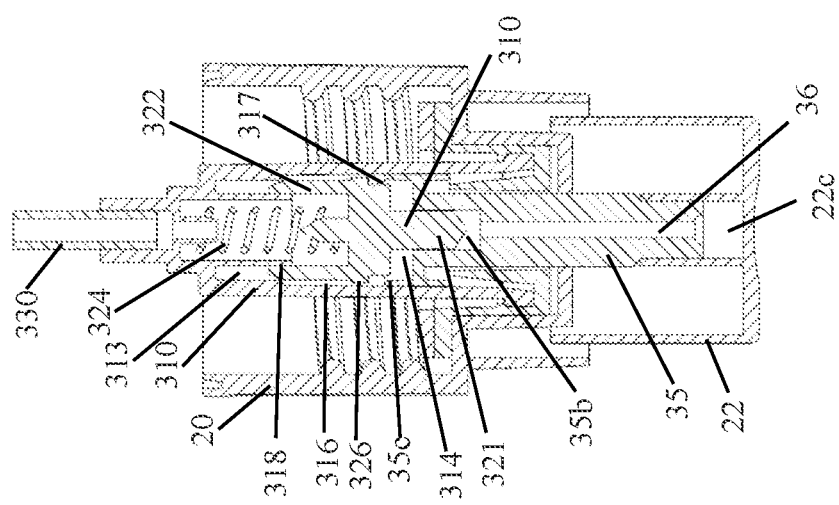
Figure 7A:
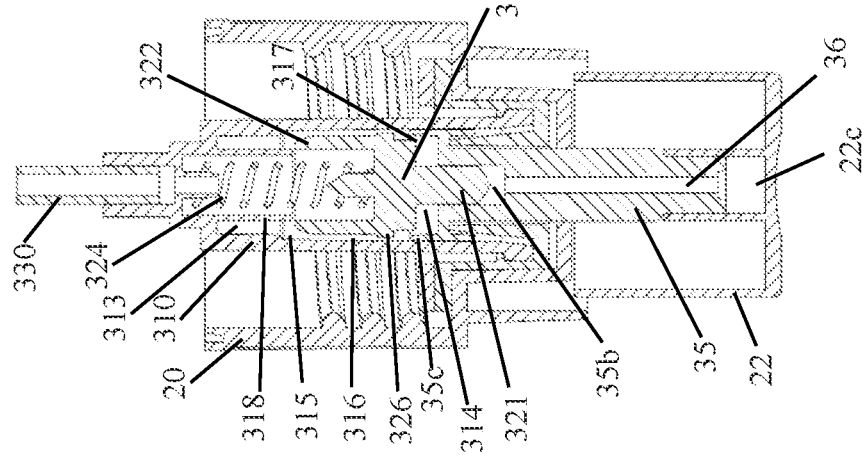

As can be concluded from the sequence of FIGS. 7a to 7c, which show three different stages of pushing the operating button 22 upwards, the cylindrical upper sealing member 322 will slide in the cylindrical slot 313 and the body of sealing member 320 will thrust the residual liquid in the piston chamber 314 via the transfer channels 316 and 317 towards the central bore 36 of the piston 35, which is always in fluid communication with the piston chamber 314. For pumping the liquid towards the outlet of the pump dispenser unit 2, the operating button 22 is thus reciprocated against the resilience resetting force of the spring 324. In the home position shown in FIGS. 6a and 6b, the piston chamber 314 is automatically refilled with liquid from the vial via the piercing mandrel 57 of vial adapter 4 (see FIG. 4a), the flexible connecting tube 330, inlet 31a, pump inlet chamber 323 and upper transfer channel 315, as the vial 7 is oriented in an upside-down orientation.

From the transfer chamber 22c of the operating button 22, the liquid will be pumped via the duct 23a of outlet member 23 and the duct 24a of tube 24 towards the outlet 26, which includes a spraying nozzle 26a.

Figure 8B:
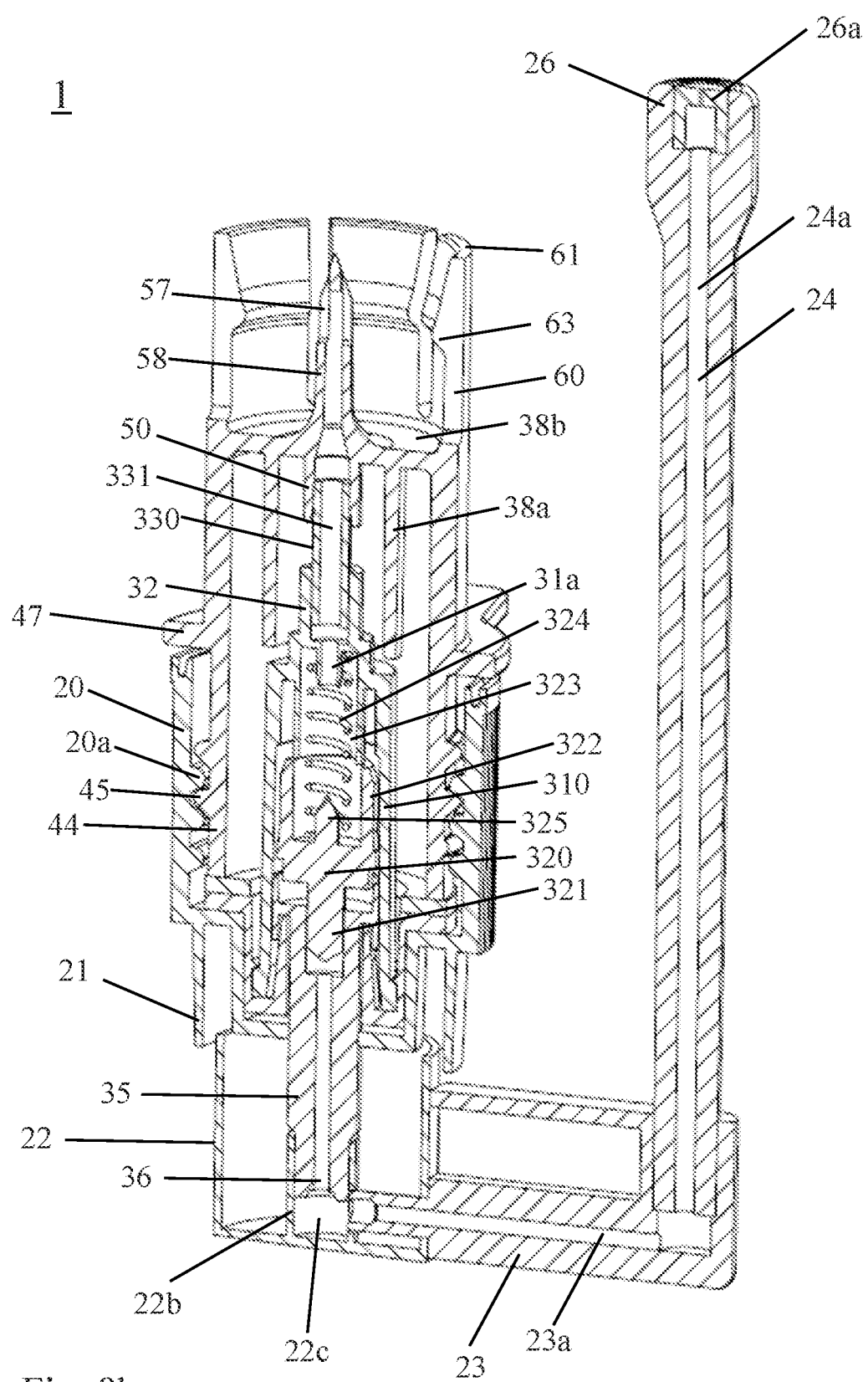
FIG. 8b is a cross-sectional view of a liquid pump dispenser of the third embodiment.

As can be concluded from FIG. 8b, the flexible connecting tube 330 that enables the fluid communication between the piercing mandrel 57 of the vial adapter and the piston housing 330 serves to compensate mechanical tolerances and any misalignment or relative displacement between the vial adapter 4 and pump dispenser unit 2 during assembly or use. One source for such a misalignment might be that in the beginning of putting the vial adapter 4 onto the front end of the medical vial the piercing mandrel 57 is slightly offset relative to the center of the vial stopper. The automatic centering effect of the resilient legs 61 of the vial adapter, described above, would then cause a slight lateral bending or deformation of the piercing mandrel 57 and neighboring parts of the vial adapter 4, such as the tube coupling portion (cylindrical side-wall) 50, when the vial adapter 4 is further pushed onto the front end of the medical vial. Another source of such a misalignment might be mechanical tolerances of the collar 20 or tubular body 48, or mistakes made during assembly of the pump dispenser 1, i.e., when connecting the vial adapter 4 with the pump dispenser unit 2. Another source of such a misalignment might be forces acting on the vial adapter 4 and pump dispenser unit 2 during use, particularly, when pushing the operating button 22 with forces having lateral force components. According to the present invention, such effects can be compensated for by providing a flexible connecting tube 330 between the vial adapter 4 and pump dispenser unit 2. As the material of the connecting tube 330 is flexible and softer than the neighboring portions of the respective tube coupling structure, a fluid-tightness of the interconnection can be ensured under all such circumstances. In the upright orientation of the medical vial the pump dispenser unit can be operated conveniently and without problems such as leakage or dripping at an outlet nozzle, because it uses a piston-type pump. The piston-type pump also ensures a precise dosage of the liquid pumped out of the medical vial.

As will become apparent to the skilled person, a further related aspect of the present invention relates to a vial adapter as outlined above for dispensing a liquid from a medical vial by first coupling the vial adapter with a pump dispenser unit, as outlined above, then latching the vial adapter to the neck of the medical vial, then bringing the resulting liquid pump dispenser and the vial into an upside-down orientation of the medical vial and then pushing the operating button of the pump dispenser unit. Another related aspect of the present invention relates to a method for dispensing a liquid from a medical vial as outlined above.

While the preferred embodiments of the present invention have been described so as to enable one skilled in the art to practice the device of the present invention, it is to be understood that variations and modifications may be employed without departing from the concept and intent of the present invention as defined in the appended claims. Accordingly, the preceding description is intended to be exemplary and should not be used to limit the scope of the invention. The scope of the invention should be determined only by reference to the appended claims.

LIST OF REFERENCE NUMERALS 1 pump dispenser
2 pump dispenser unit
4 vial adapter
7 vial
10 packaging
20 collar
20a thread
20b upper side-wall of collar 20
20c intermediate bottom of collar 20
20d bottom side-wall of collar 20
20e bottom of collar 20
21 main body
22 operating button
22a bottom of operating button 22
22b supporting cylinder
22c transfer chamber
23 outlet member
23a duct of outlet member 23
24 tube
24a duct of tube 24
25 collar
26 outlet
26a spraying nozzle
30 connecting tube
31 upper portion
31a transfer channel
32 lower portion
33 beveled front end
34 transfer channel
35 piston
35a step
35b central bore of piston 35
35c upper side-wall of piston 35
35d transfer chamber of piston 35
35e bottom of transfer chamber 35d
36 channel
38a intermediate cylinder
38b bottom
300 holding ring
301 holding arm
302 outer side-wall of holding member 301
303 inner side-wall of holding member 301
305 latching protrusion
306 cylindrical cavity
310 central cylinder/piston housing
311 side-wall of central cylinder 310
312 latching portion of central cylinder 310
313 guiding slot
314 piston chamber
315 upper transfer channel
316 transfer channel
317 transfer channel
318 inner cylinder/partition wall
320 sealing member
321 supporting member
322 upper sealing member
323 pump inlet chamber
324 spring
325 spring supporting member
326 protrusion
330 connecting tube
331 duct of connecting tube 330
40 upper coupling portion
41 main body
42 lower coupling portion
44 cylindrical portion
45 thread
46 cavity
47 finger rest
48 tubular body
49 partition wall
50 outer cylinder
51 inner cylinder
52 chamfered edge
53 double-wall cavity
53a free space
54 transfer channel
55 top wall
56a first (upper) half-space
56b second (lower) half-space
57 piercing mandrel
57a stem of piercing mandrel 57
58 cannula
59 inlet channel
60 skirt
61 resilient leg
62 slot
63 locking protrusion
64 bottom end
70 vial body
71 vial bottom
73 shoulder
74 neck
75 rolled edge of vial
75a mouth of vial 7
76 rubber stopper
76a piercing portion
76h channel
77 metal cap
77a upper ring
77b side-wall
77c locking ring
78 central hole
100 main body
101 bottom
102 flange
104 sealing foil
105 flap

The invention claimed is:
1. A liquid pump dispenser (1), for pumping a dosage of liquid from a necked vial (7), which is sealed by a stopper (76), to an outlet (26) in an upside-down orientation of the vial (7), comprising a vial adapter (4) and a pump dispenser unit (2),
wherein the vial adapter (4) comprises:
a hollow tubular body (48) having a first end (44) and a second end (64) opposite to the first end, a cavity (46) formed inside the hollow tubular body (48), a first connecting structure (45) at the first end (44) of the hollow tubular body (48), configured for connecting the vial adapter (4) with the pump dispenser unit (2), a second connecting structure (61, 63) at the second end (64) of the hollow tubular body (48), configured for latching the vial adapter (4) at a neck of the vial (7), for connecting the vial adapter (4) with the vial (7), a partition wall (49) provided inside the hollow tubular body (48), which separates the cavity (46) into a first half-space (56a) and a second half-space (56b), a piercing mandrel (57) configured for piercing the stopper (76) of the vial (7) for liquid transfer, which is disposed on the partition wall (49) in the second half-space (56b) and comprises a cannula (58) being in fluid communication with the first half-space (56a), and a first tube coupling structure (50, 51) provided on the partition wall (49) in the first half-space (56a); and wherein the pump dispenser unit (2) comprises:

a collar (20) having a connecting structure (20a) mated to the first connecting structure (45) of the vial adapter (4), for connecting the pump dispenser unit (2) with the vial adapter (4), a central pump housing (300) disposed in the collar (20), which defines a piston chamber (313, 314), in which a piston (35) is movably supported, a second tube coupling structure (32) provided at a first end of the central pump housing (300), and an operating button (22) disposed at a second end of the central pump housing (300) opposite to said first end, for actuating the piston (35), said operating button (22) being biased towards a home position and being movable relative to the collar (20) against a resilient resetting force; wherein a connecting tube (31, 330) is accommodated in at least one of the first tube coupling structure (50, 51) and second tube coupling structure (32) in a fluid-tight manner, for connecting the vial adapter (4) and the pump dispenser unit (2) for liquid transfer, and the connecting tube (31, 330) is flexible.

2. The liquid pump dispenser as claimed in claim 1, wherein the connecting tube (31, 330) is a separate member, not being integrally formed with the vial adapter (4) or pump dispenser unit (2).

3. The liquid pump dispenser as claimed in claim 1, wherein the first and second tube coupling structure (50, 51; 32) each comprises a cylindrical side-wall (50, 32) forming a cylindrical cavity of a width corresponding to an outer diameter of the connecting tube (31, 330), for accommodating a respective front end of the connecting tube (31, 330) in a fluid-tight manner.

4. The liquid pump dispenser as claimed in claim 3, wherein an outer diameter of the connecting tube (31, 330) is slightly larger than an inner width of the first and second tube coupling structure (50, 51; 32), so that the connecting tube (31, 330) is slightly compressed in the first and second tube coupling structure (50, 51; 32).

5. The liquid pump dispenser as claimed in claim 3, wherein an upper edge (52) on the inner surface of the cylindrical side-wall (50, 32) is beveled inward, for guiding a respective end of the connecting tube (31, 330) into the respective cylindrical cavity.

6. The liquid pump dispenser as claimed in claim 3, wherein
a height of the cylindrical cavity formed by the respective cylindrical side-wall (50, 32) is dimensioned such that a free space (53a) remains between the front end of the connecting tube (31, 330) and an upper surface of the partition wall (49) and/or first end of the central pump housing (300).

7. The liquid pump dispenser as claimed in claim 6, wherein
a wall thickness of the respective front end of the connecting tube (31, 330) is smaller to form a lower portion (32) of the connecting tube (31, 330), and
the height of the cylindrical cavity formed by the respective cylindrical side-wall (50, 32) is dimensioned such that the respective front end (32) of the connecting tube (31, 330) does not completely dip into the respective cylindrical cavity.

8. The liquid pump dispenser as claimed in claim 6, wherein an inner surface of the respective front end of the connecting tube (31, 330) is beveled, for guiding the respective front end of the connecting tube (31, 330) into the respective cylindrical cavity when the pump dispenser unit (2) is coupled to the vial adapter (4).

9. The liquid pump dispenser as claimed in claim 1, wherein
the piercing mandrel (57) does not protrude beyond the second end (64) of the hollow tubular body (48) of the vial adapter (4).

10. The liquid pump dispenser as claimed in claim 9, wherein
the second connecting structure comprises a plurality of resilient legs (61) disposed along a circumference of the vial adapter (4) at the second end of the hollow tubular body (48) at equiangular spacing and spaced apart to each other via axial slots (62),
the resilient legs (61) each comprise a protrusion (63) beveled inward into the second half-space (56b), and
a height, where an inner diameter of a circle formed by the beveled protrusions (63) corresponds to an outer diameter of a cap (77) provided on a front end of the vial (7), corresponds to or is less than the height of a front end of the piercing mandrel (57) above the second end of the hollow tubular body (48) of the vial adapter (4).

11. The liquid pump dispenser as claimed in claim 10, wherein the height of the front end of the piercing mandrel (57) above the second end of the hollow tubular body (48) of the vial adapter (4) is in the range of 0.4 to 2.0 mm.

12. The liquid pump dispenser as claimed in claim 10, wherein the height of the front end of the piercing mandrel (57) above the level, where the inner diameter of a circle formed by the beveled protrusions (63) corresponds to the outer diameter of the cap (77) provided on a front end of the vial (7), is in the range of 0.4 to 2.0 mm.

13. The liquid pump dispenser as claimed in claim 1, wherein the piston (35) is supported on the operating button (22) and a sealing member (320) is supported on the piston (35); wherein
in the home position of the operating button (22), the inlet (34) of the piston chamber is in fluid communication with an upper portion (313) of the piston chamber via an upper transfer channel (315),
when the operating button (22) is pushed from the home position towards the collar (20) against the resilient resetting force, the upper transfer channel (315) is sealed against the inlet (34) of the piston chamber by an upper end (322) of the sealing member (320) while the piston chamber remains in fluid communication with the outlet (36) of the central pump housing (300) via a transfer channel (316, 317) formed between the sealing member (320) and an inner side-wall of the piston chamber.

14. The liquid pump dispenser as claimed in claim 13, wherein
the upper end of the sealing member (320) is formed by a cylindrical side-wall (322), and
a cylindrical partition wall (318) is provided at an upper end of the piston chamber, to form a cylindrical slot of a width corresponding to the width of the cylindrical side-wall (322) of the sealing member (320), wherein
the upper transfer channel (315) is a narrow gap between the cylindrical side-wall (322) of the sealing member (320) and the cylindrical partition wall (318), when the operating button (22) is in the home position.

15. The liquid pump dispenser as claimed in claim 13, wherein a bottom end of the sealing member (320) is a cylindrical protrusion, which is accommodated in a central bore (35b) of the piston (35) so as to be stationary relative to the piston (35).

16. The liquid pump dispenser as claimed in claim 15, wherein the operating button (22) is in fluid communication with the outlet (26) and with an outlet (36) of the central pump housing (300), and the pump dispenser unit (2) comprises a tube (24) that is pivotably supported on the operating button (22) or on a main body (21) of the pump dispenser unit (2), wherein the outlet (26) is a spraying nozzle (26a) for spraying the liquid pumped out of the vial (7).

17. A liquid pump dispenser (1), for pumping a dosage of liquid from a necked vial (7), which is sealed by a stopper (76), to an outlet (26), said liquid pump dispenser (1) comprising a vial adapter (4) and a pump dispenser unit (2), wherein the vial adapter (4) comprises:
a hollow tubular body (48) having a first end (44) and a second end (64) opposite to the first end,
a cavity (46) formed inside the hollow tubular body (48) and divided into a first half-space (56a) and a second half-space (56b) by a partition wall (49),
a first connecting structure (45) at the first end (44) of the hollow tubular body (48), configured for connecting the vial adapter (4) with the pump dispenser unit (2),
a second connecting structure (61, 63) at the second end (64) of the hollow tubular body (48), configured for latching the vial adapter (4) at a neck of the vial (7), for connecting the vial adapter (4) with the vial (7),
a piercing mandrel (57) configured for piercing the stopper (76) of the vial (7) for liquid transfer, said piercing mandrel (57) extending through the partition wall (49), and
a first tube coupling structure (50, 51) connected with the piercing mandrel (57); and
wherein the pump dispenser unit (2) comprises:
a collar (20) having a connecting structure (20a) mated to the first connecting structure (45) of the vial adapter (4), for connecting the pump dispenser unit (2) with the vial adapter (4),
a central pump housing (300) disposed in the collar (20), which defines a piston chamber (313, 314), in which a piston (35) is movably supported,
a second tube coupling structure (32) provided at a first end of the central pump housing (300), and
an operating button (22) disposed at a second end of the central pump housing (300) opposite to said first end, for actuating the piston (35); wherein
a connecting tube (31, 330) is accommodated in at least one of the first tube coupling structure (50, 51) and second tube coupling structure (32) in a fluid-tight manner, for connecting the vial adapter (4) and the pump dispenser unit (2) for liquid transfer; wherein the connecting tube (31, 330) is flexible, and
the pump dispenser unit (2) comprises a ball-less pump actuated by the operating button (22), so that a dosage of liquid can be pumped from the necked vial (7) to the outlet (26) in an upside-down orientation of the vial (7) without leakage or dripping problems.

18. The liquid pump dispenser as claimed in claim 17, wherein the operating button (22) is biased towards a home position and movable relative to the collar (20) against a resilient resetting force, and the piston (35) is supported on the operating button (22) and a sealing member (320) is supported on the piston (35); wherein
in the home position of the operating button (22), the inlet (34) of the piston chamber is in fluid communication with an upper portion (313) of the piston chamber via an upper transfer channel (315),
when the operating button (22) is pushed from the home position towards the collar (20) against the resilient resetting force, the upper transfer channel (315) is sealed against the inlet (34) of the piston chamber by an upper end (322) of the sealing member (320) while the piston chamber remains in fluid communication with the outlet (36) of the central pump housing (300) via a transfer channel (316, 317) formed between the sealing member (320) and an inner side-wall of the piston chamber.

19. The liquid pump dispenser as claimed in claim 18, wherein
the upper end of the sealing member (320) is formed by a cylindrical side-wall (322), and
a cylindrical partition wall (318) is provided at an upper end of the piston chamber, to form a cylindrical slot of a width corresponding to the width of the cylindrical side-wall (322) of the sealing member (320), wherein
the upper transfer channel (315) is a narrow gap between the cylindrical side-wall (322) of the sealing member (320) and the cylindrical partition wall (318), when the operating button (22) is in the home position, and
a bottom end of the sealing member (320) is a cylindrical protrusion, which is accommodated in a central bore (35b) of the piston (35) so as to be stationary relative to the piston (35).

20. A liquid pump dispenser (1), for pumping a dosage of liquid from a necked vial (7), which is sealed by a stopper (76), to an outlet (26), said liquid pump dispenser (1) comprising a vial adapter (4) and a pump dispenser unit (2), each comprising a connecting structure (45, 61, 63, 20a) configured for coupling the vial adapter (4) with the pump dispenser unit (2) and the vial adapter (4) with the neck of the vial (7), respectively,
wherein the vial adapter (4) comprises:
a hollow tubular body (48) having a first end (44) and a second end (64) opposite to the first end,
a cavity (46) formed inside the hollow tubular body (48) and divided into a first half-space (56a) and a second half-space (56b) by a partition wall (49), and
a piercing mandrel (57) configured for piercing the stopper (76) of the vial (7) for liquid transfer when the vial adapter (4) is coupled with the neck of the vial (7), said piercing mandrel (57) extending through the partition wall (49); and wherein the pump dispenser unit (2) comprises:
- a central pump housing (300), which defines a piston chamber (313, 314), in which a piston (35) is movably supported, and
- an operating button (22) disposed at a second end of the central pump housing (300) opposite to said first end, for actuating the piston (35); wherein
- the piercing mandrel (57) is connected with the pump dispenser unit (2) via a connecting tube (31, 330) in a fluid-tight manner for liquid transfer; wherein the connecting tube (31, 330) is flexible, and the pump dispenser unit (2) comprises a ball-less pump actuated by the operating button (22), so that a dosage of liquid can be pumped from the necked vial (7) to the outlet (26) in an upside-down orientation of the vial (7) without leakage or dripping problems.

\* \* \* \* \*